United States Patent
Narendranath

(10) Patent No.: US 9,034,620 B2
(45) Date of Patent: May 19, 2015

(54) SYSTEM FOR THE TREATMENT OF BIOMASS TO FACILITATE THE PRODUCTION OF ETHANOL

(75) Inventor: Neelakantam V. Narendranath, Sioux Falls, SD (US)

(73) Assignee: POET RESEARCH, INC., Sioux Falls, SD (US)

( * ) Notice: Subject to any disclaimer, the term of this patent is extended or adjusted under 35 U.S.C. 154(b) by 0 days.

(21) Appl. No.: 13/638,253

(22) PCT Filed: Mar. 18, 2011

(86) PCT No.: PCT/US2011/029050
§ 371 (c)(1),
(2), (4) Date: Sep. 28, 2012

(87) PCT Pub. No.: WO2011/116320
PCT Pub. Date: Sep. 22, 2011

(65) Prior Publication Data
US 2013/0143290 A1 Jun. 6, 2013

Related U.S. Application Data

(60) Provisional application No. 61/315,833, filed on Mar. 19, 2010.

(51) Int. Cl.
C12P 7/10 (2006.01)
C12P 19/02 (2006.01)
C12P 19/14 (2006.01)
C12M 1/00 (2006.01)
C12M 1/33 (2006.01)

(52) U.S. Cl.
CPC . *C12P 7/10* (2013.01); *C12P 19/02* (2013.01); *C12P 19/14* (2013.01); *C12P 2201/00* (2013.01); *Y02E 50/16* (2013.01); *C12M 21/12* (2013.01); *C12M 45/02* (2013.01); *C12M 45/04* (2013.01); *C12M 45/06* (2013.01)

(58) Field of Classification Search
None
See application file for complete search history.

(56) References Cited

U.S. PATENT DOCUMENTS

| | | |
|---|---|---|
| 3,212,932 A | 10/1965 | Hess et al. |
| 4,014,743 A | 3/1977 | Black |
| 4,029,515 A | 6/1977 | Kiminki et al. |
| 4,152,197 A | 5/1979 | Lindahl et al. |
| 4,168,988 A | 9/1979 | Riehm et al. |
| 4,342,831 A | 8/1982 | Faber et al. |
| 4,425,433 A | 1/1984 | Neves |
| 4,427,453 A | 1/1984 | Reitter |
| 4,432,805 A | 2/1984 | Nuuttila et al. |
| 4,461,648 A | 7/1984 | Foody |
| 4,529,699 A | 7/1985 | Gerez et al. |
| 4,552,616 A | 11/1985 | Kauppi |
| 4,612,286 A | 9/1986 | Sherman et al. |
| 4,668,340 A | 5/1987 | Sherman |
| 4,752,579 A | 6/1988 | Arena et al. |
| 4,908,098 A | 3/1990 | DeLong et al. |
| 4,941,944 A | 7/1990 | Chang |
| 4,997,488 A | 3/1991 | Gould et al. |
| 5,125,977 A | 6/1992 | Grohmann et al. |
| 5,171,592 A | 12/1992 | Holtzapple et al. |
| 5,221,357 A | 6/1993 | Brink |
| 5,328,562 A | 7/1994 | Rafferty et al. |
| 5,338,366 A | 8/1994 | Grace et al. |
| 5,366,558 A | 11/1994 | Brink |
| 5,370,999 A | 12/1994 | Stuart |
| 5,411,594 A | 5/1995 | Brelsford |
| 5,424,417 A | 6/1995 | Torget et al. |
| 5,498,766 A | 3/1996 | Stuart et al. |
| 5,536,325 A | 7/1996 | Brink |
| 5,562,777 A | 10/1996 | Farone et al. |
| 5,580,389 A | 12/1996 | Farone et al. |
| 5,597,714 A | 1/1997 | Farone et al. |
| 5,628,830 A | 5/1997 | Brink |

(Continued)

FOREIGN PATENT DOCUMENTS

| | | |
|---|---|---|
| EP | 0 044 658 | 1/1982 |
| EP | 0 098 490 | 1/1984 |

(Continued)

OTHER PUBLICATIONS

Cara et al. "Influence of solid loading on enzymatic hydrolysis of steam expoleded or liquid hot water treated olive tree biomass" Process Biochemistry (2007) 42:1003-1009.*
Li et al. "Two cellulases, CelA and CelC from polycentric anaerobic fungus *Orpionmyces* strain PC-2 contain N-terminal docking domains for a cellulase-hemicellulase complex" Applied and Environmental Microbiology (1997) 63:4721-4728.*
Gao et al. "Strategy for identification of novel fungal and bacterial glycosyl hydrolase hybrid mixtures that can efficiently sccharify pretreated lignocellulosic biomass" (2010)Bioenerg, Res. 3:67-81.*
Cara et al "Influence of solid loading on enzymatic hydrolysis of steam exploded or liquid hot water treated olive tree biomass" Procee Biochemistry (2007) 42:1003-1009.*

(Continued)

*Primary Examiner* — Manjunath Rao
*Assistant Examiner* — Samuel Liu
(74) *Attorney, Agent, or Firm* — Kagan Binder, PLLC

(57) ABSTRACT

A method for treating biomass to be supplied to a fermentation system for the production of a fermentation product is disclosed. The method comprises the steps of pre-treating the biomass into pre-treated biomass; separating the pre-treated biomass into a first component comprising glucan and a second component comprising sugars; providing a combined component comprising at least a portion of the first component and at least a portion of the second component; and treating the combined component of the pre-treated biomass into a treated component comprising glucose by application of an enzyme formulation. A system for treating biomass to be supplied to a fermentation system for the production of a fermentation product is also disclosed. The system comprises an apparatus configured to pre-treat the biomass; a separator configured to separate the pre-treated biomass; and a vessel configured to contain a combined component.

30 Claims, 20 Drawing Sheets

(56) References Cited

U.S. PATENT DOCUMENTS

| | | |
|---|---|---|
| 5,693,296 A | 12/1997 | Holtzapple et al. |
| 5,705,369 A * | 1/1998 | Torget et al. ............... 435/105 |
| 5,711,817 A | 1/1998 | Titmas |
| 5,726,046 A | 3/1998 | Farone et al. |
| 5,733,758 A | 3/1998 | Nguyen |
| 5,769,934 A | 6/1998 | Ha et al. |
| 5,782,982 A | 7/1998 | Farone et al. |
| 5,820,687 A | 10/1998 | Farone et al. |
| 5,865,898 A | 2/1999 | Holtzapple et al. |
| 5,879,463 A | 3/1999 | Proenca |
| 5,916,780 A | 6/1999 | Foody et al. |
| 5,932,452 A | 8/1999 | Mustranta et al. |
| 5,932,456 A | 8/1999 | Van Draanen et al. |
| 5,972,118 A | 10/1999 | Hester et al. |
| 5,975,439 A | 11/1999 | Chieffalo et al. |
| 6,022,419 A | 2/2000 | Torget et al. |
| 6,090,595 A | 7/2000 | Foody et al. |
| 6,228,177 B1 | 5/2001 | Torget |
| 6,379,504 B1 | 4/2002 | Miele et al. |
| 6,419,788 B1 | 7/2002 | Wingerson |
| 6,423,145 B1 | 7/2002 | Nguyen et al. |
| 6,555,350 B2 | 4/2003 | Ahring et al. |
| 6,620,292 B2 | 9/2003 | Wingerson |
| 6,660,506 B2 | 12/2003 | Nguyen et al. |
| 6,692,578 B2 | 2/2004 | Schmidt et al. |
| 6,770,168 B1 | 8/2004 | Stigsson |
| 7,198,925 B2 | 4/2007 | Foody |
| 7,238,242 B2 | 7/2007 | Pinatti et al. |
| 7,354,743 B2 | 4/2008 | Vlasenko et al. |
| 7,455,997 B2 | 11/2008 | Hughes |
| 7,501,025 B2 | 3/2009 | Bakker et al. |
| 7,503,981 B2 | 3/2009 | Wyman et al. |
| 7,585,652 B2 | 9/2009 | Foody et al. |
| 7,604,967 B2 | 10/2009 | Yang et al. |
| 7,649,086 B2 | 1/2010 | Belanger et al. |
| 7,666,637 B2 | 2/2010 | Nguyen |
| 7,670,813 B2 | 3/2010 | Foody et al. |
| 7,709,042 B2 | 5/2010 | Foody et al. |
| 7,754,456 B2 | 7/2010 | Penttila et al. |
| 7,754,457 B2 | 7/2010 | Foody et al. |
| 7,807,419 B2 | 10/2010 | Hennessey et al. |
| 7,815,741 B2 | 10/2010 | Olson |
| 7,815,876 B2 | 10/2010 | Olson |
| 7,819,976 B2 | 10/2010 | Friend et al. |
| 7,875,444 B2 | 1/2011 | Yang et al. |
| 7,901,511 B2 | 3/2011 | Griffin et al. |
| 8,057,639 B2 | 11/2011 | Pschorn et al. |
| 8,057,641 B2 | 11/2011 | Bartek et al. |
| 8,110,383 B2 * | 2/2012 | Jonsson et al. ............... 435/161 |
| 8,123,864 B2 | 2/2012 | Christensen et al. |
| 8,288,600 B2 | 10/2012 | Bartek et al. |
| 8,449,728 B2 | 5/2013 | Redford |
| 8,815,552 B2 | 8/2014 | Narendranath et al. |
| 2002/0192774 A1 | 12/2002 | Ahring et al. |
| 2004/0060673 A1 | 4/2004 | Phillips et al. |
| 2005/0069998 A1 | 3/2005 | Ballesteros Perdices et al. |
| 2006/0281157 A1 | 12/2006 | Chotani et al. |
| 2008/0026431 A1 | 1/2008 | Saito et al. |
| 2008/0057555 A1 | 3/2008 | Nguyen |
| 2008/0277082 A1 | 11/2008 | Pschorn et al. |
| 2008/0295981 A1 | 12/2008 | Shin et al. |
| 2009/0308383 A1 | 12/2009 | Shin et al. |
| 2010/0003733 A1 | 1/2010 | Foody et al. |
| 2010/0144001 A1 | 6/2010 | Horton |
| 2010/0233771 A1 | 9/2010 | McDonald et al. |
| 2010/0285553 A1 | 11/2010 | Delmas et al. |
| 2011/0079219 A1 | 4/2011 | McDonald et al. |
| 2011/0094505 A1 | 4/2011 | Bulla et al. |
| 2011/0171708 A1 | 7/2011 | Larsen |
| 2012/0129234 A1 | 5/2012 | McDonald et al. |
| 2012/0138246 A1 | 6/2012 | Christensen et al. |
| 2012/0201947 A1 | 8/2012 | Stuart |
| 2013/0065289 A1 | 3/2013 | Carlson |
| 2013/0337521 A1 | 12/2013 | Carlson et al. |
| 2014/0024826 A1 | 1/2014 | Narendranath et al. |
| 2014/0209092 A1 | 7/2014 | McDonald et al. |
| 2014/0234911 A1 | 8/2014 | Narendranath et al. |

FOREIGN PATENT DOCUMENTS

| | | |
|---|---|---|
| EP | 0 159 795 | 10/1985 |
| EP | 0 884 391 | 12/1998 |
| EP | 1 259 466 | 11/2002 |
| EP | 1 130 085 | 10/2005 |
| FR | 2 397 486 | 2/1979 |
| FR | 2 609 046 | 7/1988 |
| WO | WO 94/08027 | 4/1994 |
| WO | WO 94/29475 | 12/1994 |
| WO | WO 95/08648 | 3/1995 |
| WO | WO 98/14270 | 4/1998 |
| WO | WO 98/56958 | 12/1998 |
| WO | WO 99/06133 | 2/1999 |
| WO | WO 00/14120 | 3/2000 |
| WO | WO 00/61858 | 10/2000 |
| WO | WO 00/73221 | 12/2000 |
| WO | WO 01/32715 | 5/2001 |
| WO | WO 01/60752 | 8/2001 |
| WO | WO 02/14598 | 2/2002 |
| WO | WO 02/24882 | 3/2002 |
| WO | WO 02/38786 | 5/2002 |
| WO | WO 02/051561 | 7/2002 |
| WO | WO 02/067691 | 9/2002 |
| WO | WO 02/070753 | 9/2002 |
| WO | WO 03/013714 | 2/2003 |
| WO | WO 03/071025 | 8/2003 |
| WO | WO 03/078644 | 9/2003 |
| WO | WO 2004/081193 | 9/2004 |
| WO | WO 2005/099854 | 10/2005 |
| WO | WO 2005/118828 | 12/2005 |
| WO | WO 2006/032282 | 3/2006 |
| WO | WO 2006/034590 | 4/2006 |
| WO | WO 2006/056838 | 6/2006 |
| WO | 2006101832 A2 | 9/2006 |
| WO | WO 2007/009463 | 1/2007 |
| WO | WO 2008/095098 | 8/2008 |
| WO | WO 2008/131229 | 10/2008 |
| WO | WO 2009/003167 | 12/2008 |
| WO | WO 2010/113129 * | 3/2009 ............... C12P 12/02 |
| WO | WO 2009/045651 | 4/2009 |
| WO | WO 2009/108773 | 9/2009 |
| WO | WO 2010/071805 | 6/2010 |
| WO | 2010113129 A2 | 10/2010 |
| WO | WO 2010/113130 | 10/2010 |
| WO | WO 2011/061400 | 5/2011 |
| WO | WO 2011/116317 | 9/2011 |
| WO | WO 2011/159915 | 12/2011 |
| WO | WO 2012/042497 | 4/2012 |
| WO | WO 2012/042498 | 4/2012 |
| WO | WO 2012/103281 | 8/2012 |
| WO | WO 2012/131665 | 10/2012 |

OTHER PUBLICATIONS

Li et al. "Two cellulases CeIA and CeIC from polycentric anaerobic fungus *Orpionmyces* strain PC-2 contain N-terminal docking domains for a cellulase-mekicellulase complex" Applied and Environmental Microbiology (1997) 63:4721-4728.*

Gao et al. "Strategy for identification of novel fungal and bacterial glycosyl hydrolase hybrid mixtures tha can efficiently saccharify pretreated lignocellulosic biomass" Bioeng. Res. (2010) 3:67-81.*

Olsson et al. "Fermentation of lignocellulosic hydrolysates for ethanol production" Enzyme and Microbial Technology (1996) 18:312-331.*

Guo et al. "Characterization of enzymatic saccharification for ac-d-pretreated lignicellulosic materials with different lignin composition" Enzyme and Microbial Technology (2009) 45:80-87.*

Bura et al. "Influence of Xylan on the enzymatic hydrolysis of steam-pretreated corn stover and hybrid poplar" Biotechnol. Prog. (2009) 25 315-322.*

(56) References Cited

OTHER PUBLICATIONS

Xiao et al. "Effects of sugar inhibition on cellulases and b-glucosidase during enzymatic hydrolysis of softwood substrates" Applied Biochemistry and Biotechnology (2004) 113-116:1115-1126.*
Kumar et al. "Recent advances in production of bioethanol from lignocellulosic biomass" Chem Eng Technol 2009 32, 517-526.*
Adney, B. et al., "Measurement of Cellulase Activities", Technical Report NREL/TP-510-42628 (2008) Cover; p. 1-8.
Caparros, S. et al., "Xylooligosaccharides Production from *Arundo donax*", J. Agric. Food Chem. 55 (2007): p. 5536-5543.
Cort, J. et al., "Minimize Scale-Up Risk", www.aiche.org/cep, (2010): p. 39-49.
Demain, A.L. et al., "Cellulase, Clostridia, and Ethanol", Microbiology and Molecular Biology Reviews 69(1) (2005): p. 124-154.
Dien, B.S. et al., "Enzyme characterization for hydrolysis of AFEX and liquid hot-water pretreated distillers' grains and their conversion to ethanol", Bioresource Technology 99 (2008): p. 5216-5225.
Gibbons, W.R. et al., "Fuel Ethanol and High Protein Feed from Corn and Corn-Whey Mixtures in a Farm-Scale Plant", Biotechnology and Bioengineering XXV (1983): p. 2127-2148.
Goodman, B. J., "FY 1988 Ethanol from Biomass Annual Report" (1989): p. 1-458.
Grohmann, K. et al., "Optimization of Dilute Acid Pretreatment of Biomass", Biotechnology and Bioengineering Symp. 15 (1985): p. 59-80.
Grohmann, K. et al., "Dilute Acid Pretreatment of Biomass at High Solids Concentrations", Biotechnology and Bioengineering Symp. 17 (1986): p. 135-151.
Humbird, D. et al., "Process Design and Economics for Biochemical Conversion of Lignocellulosic Biomass to Ethanol: Dilute-Acid Pretreatment and Enzymatic Hydrolysis of Corn Stover", National Renewable Energy Laboratory (2011): Covers with Introduction; p. 1-114.
Jeoh, T. "Steam Explosion Pretreatment of Cotton Gin Waste for Fuel Ethanol Production", Thesis submitted to Virginia Polytechnic Institute and State University (1998): Cover with Introduction; p. 1-138.
Jorgensen, H. et al., "Enzymatic conversion of lignocellulose into fermentable sugars: challenges and opportunities", Biofuels, Bioprod. Bioref. 1 (2001): p. 119-134.
Kumar, R. et al., "Effect of Enzyme Supplementation at Moderate Cellulase Loadings on Initial Glucose and Xylose Release from Corn Stover Solids Pretreated by Leading Technologies", Biotechnology and Bioengineering 102(2)(2009): p. 457-467.
Lynd, L.R. et al. "Consolidated bioprocessing of cellulosic biomass: an update", Current Opinion in Biotechnology 16 (2005): p. 577-583.
Mosier, N. et al., "Features of promising technologies for pretreatment of lignocellulosic biomass", Bioresource Technology 96 (2005): p. 673-686.
McMillan, J.D. "Processes for Pretreating Lignocellulosic Biomass: A Review", National Renewable Energy Laboratory (1992): Covers with Introduction; p. 1-44.
Nandini, C. et al. "Carbohydrate composition of wheat, wheat bran, *Sorghum* and bajra with good chapatti/roti (Indian flat bread) making quality", Food Chemistry 73 (2001): p. 197-203.
Sanchez, O.J. et al., "Trends in biotechnological production of fuel ethanol from different feedstocks", Bioresource Technology 99 (2008): p. 5270-5295.
Saska, M. et al., "Aqueous Extraction of Sugarcane Bagasse Hemicellulose and Production of Xylose Syrup", Biotechnology and Bioengineering 45 (1995): p. 517-523.
Sepulveda-Huerta, E. et al. "Production of detoxified sorghum straw hydrolysates for fermentative purposes", Journal of the Science of Food and Agriculture 86 (2006): p. 2579-2586.
Spindler, D. et al., "Evaluation of Pretreated Woody Crops for the Simultaneous Saccharification and Fermentation Process", Ethanol from Biomass. FY 1988, Annual Report (1989): p. B33-B43.

Taherzadeh, M.J. et al., "Acid-based Hydrolysis Processes for Ethanol from Lignocellulosic Materials: A Review", BioResources 2(3) (2007): p. 472-499.
Taherzadeh, M.J. et al., "Enzyme-based Hydrolysis Processes for Ethanol from Lignocellulosic Materials: A Review", BioResources 2(4) (2007): p. 707-738.
Texeira, R.H. et al., "Ethanol Annual Report FY 1990", (1991): p. 1-346.
Torget, R. et al., "Dilute Acid Pretreatment of Short Rotation Woody and Herbaceous Crops", Applied Biochemistry and Biotechnology 24/25 (1990): p. 115-126.
Torget, R. et al., "Initial Design of a Dilute Sulfuric Acid Pretreatment Process for Aspen Wood Chips", Solar Energy Research Institute (1988): p. 89-104.
Torget, R. et al., "Dilute Acid Pretreatment of Corn Cobs, Corn Stover, and Short-Rotation Crops", FY 1990 Ethanol Annual Report (1991): p. 71-82.
Weil, J. et al., "Pretreatment of Corn Fiber by Pressure Cooking in Water", Applied Biochemistry and Biotechnology 73 (1998): p. 1-17.
Wyman, Charles E., "What is (and is not) vital to advancing cellulosic ethanol", Trends in Biotechnology 25(4) (2007): p. 153-157.
Wyman, C.E. et al., "Coordinated development of leading biomass pretreatment technologies", Bioresource Technology 96 (2005): p. 1959-1966.
Yang, B. et al., "Pretreatment: the key to unlocking low-cost cellulosic ethanol", Biofuels, Bioprod. Bioref. 2 (2008): p. 26-40.
Zhang, Y-H.P. et al., "Outlook for cellulose improvement: Screening and selection strategies", Biotechnology Advances 24 (2006): p. 452-481.
Zhang, Y.P. et al., "Toward an Aggregated Understanding of Enzymatic Hydrolysis of Cellulose: Noncomplexed Cellulase Systems", Biotechnology and Bioengineering 88(7) (2004): p. 797-824.
Larsen, et al., "The IBUS Process—Lignocellulosic Bioethanol Close to a Commercial Reality". Chemical Engineering and Technology, Weinheim, DE, vol. 21, No. 5, Apr. 22, 2008, pp. 765-772, XP002517673, ISSN: 0930-7516, DOI:10.1002/CEAT.200800048, 8 pages.
International Search Report and Written Opinion for International Application No. PCT/US2011/029050 dated Jul. 18, 2011, 12 pages.
U.S. Appl. No. 12/716,989, filed Mar. 2010, Kwiatkowski.
U.S. Appl. No. 12/827,948, filed Jun. 2010, Bootsma et al.
U.S. Appl. No. 13/209,170, filed Aug. 2011, Bly et al.
U.S. Appl. No. 14/465,177, filed Aug. 2014, Narendranath et al.
Blunk, S.L. et al. "Combustion Properties of Lignin Residue From Lignocellulose Fermentation", National Renewable Energy Laboratory, 2000, pp. 1-15.
Haagensen, F. et al. "Enzymatic Hydrolysis and Glucose Fermentation of Wet Oxidized Sugarcane Bagasse and Rice Straw for Bioethanol Production", Ris0-R-1517(EN), 2002, pp. 184-195.
Marchal, R. et al. "Large-Scale Enzymatic Hydrolysis of Agricultural Lignocellulosic Biomass. Part 2: Conversion Into Acetone-Butanol", Bioresource Technology 42, 1992, pp. 205-217.
Reith, J.H. et al. "Co-Production of Bio-Ethanol, Electricity and Heat From Biomass Residues", Contribution to the $12^{th}$ European Conference and Technology Exhibition on Biomass for Energy, Industry and Climate Protection, Jun. 17-21, 2002, Amsterdam, the Netherlands, pp. 1-22.
Sun, Y. et al. "Hyrdolysis of Lignocellulosic Materials for Ethanol Production: A Review", Bioresource Technology 83, 2002, pp. 1-11.
Thomsen, M.H. et al., "Preliminary Results on Optimization of Pilot Scale Pretreatment of Wheat Straw Used in Coproduction of Bioethanol and Electricity", Applied Biochemistry and Biotechnology, vol. 129-132, 2006, p. 448.
Varga, E., et al., "High Solid Simultaneous Saccharification and Fermentation of Wet Oxidized Corn Stover to Ethanol", Biotechnol. Bioeng. 88(5), 2004, Abstract.
U.S. Appl. No. 14/459,977, filed Aug. 2014, Bootsma.

* cited by examiner

FIG. 14A

Biomass Composition

| Cob (percent) | Husks/ Leaves (percent) | Stalk (percent) | Cellulose (Glucan) (percent) | Hemicellulose | | | | Lignin (percent) | Ash (percent) |
|---|---|---|---|---|---|---|---|---|---|
| | | | | Xylan (percent) | Arabinan (percent) | Acetate (percent) | Composite (percent) | | |
| 100 | 0 | 0 | 36.0 | 33.3 | 3.6 | 3.0 | 39.9 | 14.9 | 2.2 |
| 0 | 100 | 0 | 37.2 | 25.6 | 4.9 | 2.2 | 32.7 | 13.0 | 7.7 |
| 0 | 0 | 100 | 41.7 | 22.5 | 2.4 | 2.6 | 27.5 | 18.3 | 3.7 |
| 50 | 0 | 50 | 38.8 | 27.9 | 3.0 | 2.8 | 33.7 | 16.6 | 3.0 |
| 50 | 50 | 0 | 36.6 | 29.5 | 4.2 | 2.6 | 36.3 | 14.0 | 5.0 |
| 30 | 50 | 20 | 37.7 | 27.3 | 4.0 | 2.5 | 33.8 | 14.6 | 5.3 |

FIG. 14B

Biomass

| | Cellulose (Glucan) (percent) (approx.) | Hemicellulose (percent) (approx.) | Lignin (percent) (approx.) | Ash (percent) (approx.) |
|---|---|---|---|---|
| Typical Range | 35-45 | 24-42 | 12-20 | 2-8 |
| Expected Range | 30-55 | 20-50 | 10-25 | 1-10 |

FIG. 15A

Pre-Treated Biomass Liquid Component Composition

| Cob (percent) | Husks/ Leaves (percent) | Stalk (percent) | Glucose (percent) | Xylose (percent) | Arabinose (percent) | Acetic Acid (ppm) |
|---|---|---|---|---|---|---|
| 100 | 0 | 0 | 0.4 | 4.8 | 0.5 | 6090 |
| 0 | 100 | 0 | 0.4 | 2.7 | 0.5 | 3400 |
| 0 | 0 | 100 | 0.4 | 4.2 | 0.4 | 6180 |
| 50 | 0 | 50 | 0.4 | 4.5 | 0.4 | 6135 |
| 30 | 50 | 20 | 0.4 | 3.6 | 0.5 | 4763 |

FIG. 15B

**Pre-Treated Biomass
Liquid Component**

|  | Glucose (percent) (approx.) | Xylose (percent) (approx.) | Arabinose (percent) (approx.) | Acetic Acid (ppm) (approx.) |
|---|---|---|---|---|
| Typical Range | 0-1 | 2-6 | 0-1 | 3000-6400 |
| Expected Range | 0-1 | 1-8 | 0-1 | 2000-8000 |

FIG. 16A

**Pre-Treated Biomass
Solids Component Composition**

| Cob (percent) | Husks/ Leaves (percent) | Stalk (percent) | Cellulose (Glucan) (percent) | Hemicellulose | | | | Lignin (percent) | Ash (percent) |
|---|---|---|---|---|---|---|---|---|---|
| | | | | Xylan (percent) | Arabinan (percent) | Acetate (percent) | Composite (percent) | | |
| 100 | 0 | 0 | 60.2 | 9.5 | 0.9 | 0.3 | 10.7 | 26.7 | 1.2 |
| 0 | 100 | 0 | 54.4 | 1.3 | 0.7 | 0.7 | 10.4 | 23.8 | 9.7 |
| 0 | 0 | 100 | 51.1 | 1.4 | 1.0 | 1.0 | 15.4 | 27.3 | 3.1 |
| 50 | 0 | 50 | 55.7 | 5.5 | 0.9 | 0.6 | 13.1 | 27.0 | 2.2 |
| 50 | 50 | 0 | 57.3 | 5.4 | 0.8 | 0.5 | 10.6 | 25.2 | 5.4 |
| 30 | 50 | 20 | 55.5 | 3.8 | 0.8 | 0.6 | 11.5 | 25.4 | 5.8 |

FIG. 16B

**Pre-Treated Biomass
Solids Component**

|  | Cellulose (Glucan) (percent) (approx.) | Hemicellulose (percent) (approx.) | Lignin (percent) (approx.) | Ash (percent) (approx.) |
|---|---|---|---|---|
| Typical Range | 48-62 | 8-17 | 22-30 | 1-10 |
| Expected Range | 45-65 | 5-20 | 20-32 | 1-10 |

FIG. 17A

| Enzyme Loading (mg/g Glucan) | Glucose, 0 hr | | | Enzyme Loading (mg/g Glucan) | Xylose, 0 hr | | |
|---|---|---|---|---|---|---|---|
| | 5 Percent Solids | 10 Percent Solids | 15 Percent Solids | | 5 Percent Solids | 10 Percent Solids | 15 Percent Solids |
| 6.00 | 0.11 | 0.21 | 0.27 | 6.00 | 0.69 | 1.26 | 1.31 |
| 9.00 | 0.11 | 0.21 | 0.27 | 9.00 | 0.69 | 1.26 | 1.31 |
| 12.00 | 0.11 | 0.21 | 0.27 | 12.00 | 0.69 | 1.26 | 1.31 |
| 16.27 | 0.12 | 0.21 | 0.27 | 16.27 | 0.69 | 1.26 | 1.31 |

| Enzyme Loading (mg/g Glucan) | Glucose, 90 hr | | | Enzyme Loading (mg/g Glucan) | Xylose, 90 hr | | |
|---|---|---|---|---|---|---|---|
| | 5 Percent Solids | 10 Percent Solids | 15 Percent Solids | | 5 Percent Solids | 10 Percent Solids | 15 Percent Solids |
| 6.00 | 2.52 | 5.04 | 6.76 | 6.00 | 1.08 | 1.62 | 1.67 |
| 9.00 | 2.72 | 5.47 | 7.72 | 9.00 | 1.12 | 1.68 | 1.76 |
| 12.00 | 2.79 | 5.64 | 8.28 | 12.00 | 1.13 | 1.71 | 1.83 |
| 16.27 | 2.66 | 5.92 | 8.95 | 16.27 | 1.14 | 1.76 | 1.87 |

FIG. 17B

| Enzyme Loading (mg/g Glucan) | Glucose Released By Hydrolysis (Percent in Solution) | | |
|---|---|---|---|
| | 5 Percent Solids | 10 Percent Solids | 15 Percent Solids |
| 6.00 | 2.41 | 4.83 | 6.48 |
| 9.00 | 2.61 | 5.27 | 7.45 |
| 12.00 | 2.68 | 5.43 | 8.01 |
| 16.27 | 2.53 | 5.71 | 8.68 |
| Theoretical Glucose Yield from Glucan (Percent in Solution) | | | |
| | 3.08 | 6.91 | 10.37 |

| Enzyme Loading (mg/g Glucan) | Glucose Yield Percent of Theoretical | | |
|---|---|---|---|
| | 5 Percent Solids | 10 Percent Solids | 15 Percent Solids |
| 6.00 | 78.1 | 69.9 | 62.5 |
| 9.00 | 84.6 | 76.2 | 71.8 |
| 12.00 | 87.1 | 78.6 | 77.2 |
| 16.27 | 82.2 | 82.7 | 83.7 |

FIG. 17C

| | Glucose Yield Percent of Theoretical | |
|---|---|---|
| | C6 Stream Enzyme Loading 16.6 mg/g | C5/C6 Stream Enzyme Loading 16.27 mg/g |
| 5 Percent Solids | 81.0 | 82.2 |
| 10 Percent Solids | 82.8 | 82.7 |
| 15 Percent Solids | 83.6 | 83.7 |

FIG. 18A

| Time (h) | Glucose (percent) | Xylose (percent) | Ethanol (percent) |
|---|---|---|---|
| 0 | 12.97 | 5.50 | 0.00 |
| 24 | 0.09 | 0.67 | 9.64 |
| 48 | 0.13 | 0.64 | 9.30 |

FIG. 18B

| Time (h) | Glucose (percent) | Xylose (percent) | Ethanol (percent) |
|---|---|---|---|
| 0 | 13.87 | 4.34 | 0.00 |
| 24 | 0.10 | 0.40 | 9.67 |
| 48 | 0.12 | 0.36 | 9.52 |

FIG. 18C

| Time (h) | Glucose (percent) | Xylose (percent) | Ethanol (percent) |
|---|---|---|---|
| 0 | 13.42 | 3.08 | 0.00 |
| 24 | 0.09 | 0.21 | 8.79 |
| 48 | 0.11 | 0.19 | 8.65 |

SYSTEM FOR THE TREATMENT OF BIOMASS TO FACILITATE THE PRODUCTION OF ETHANOL

CROSS-REFERENCE TO RELATED APPLICATIONS

This application is a U.S. national stage filing of Patent Cooperation Treaty (PCT) application serial number PCT/US11/29050 entitled "SYSTEM FOR TREATMENT OF BIOMASS TO FACILITATE THE PRODUCTION OF ETHANOL" filed on Mar. 18, 2011, which claims the benefit of U.S. Provisional Application Ser. No. 61/315,833, entitled "SYSTEM FOR TREATMENT OF BIOMASS TO FACILITATE THE PRODUCTION OF ETHANOL (ENZYME HYDROLYSIS OF C6+C5 STREAM)" filed Mar. 19, 2010. The entireties of the aforementioned applications are herein incorporated by reference.

FIELD

The present invention relates to a system for treatment of biomass in the production of ethanol. The present invention also relates to a system for treatment of biomass to make sugars available for fermentation to facilitate the efficient production of ethanol.

BACKGROUND

Ethanol can be produced from grain-based feedstocks (e.g., corn, sorghum/milo, barley, wheat, soybeans, etc.), from sugar (e.g., sugar cane, sugar beets, etc.), and from biomass (e.g., from lignocellulosic feedstocks such as switchgrass, corn cobs and stover, wood, or other plant material).

Biomass comprises plant matter that can be suitable for direct use as a fuel/energy source or as a feedstock for processing into another bioproduct (e.g., a biofuel such as cellulosic ethanol) produced at a biorefinery (such as an ethanol plant). Biomass may comprise, for example, corn cobs and stover (e.g., stalks and leaves) made available during or after harvesting of the corn kernels, fiber from the corn kernel, switchgrass, farm or agricultural residue, wood chips or other wood waste, and other plant matter (grown for processing into bioproducts or for other purposes). In order to be used or processed, biomass will be harvested and collected from the field and transported to the location where it is to be used or processed.

In a conventional ethanol plant producing ethanol from corn, ethanol is produced from starch. Corn kernels are cleaned and milled to prepare starch-containing material for processing. (Corn kernels can also be fractionated to separate the starch-containing material (e.g., endosperm) from other matter (e.g., fiber and germ).) The starch-containing material is slurried with water and liquefied to facilitate saccharification where the starch is converted into sugar (e.g., glucose) and fermentation where the sugar is converted by an ethanologen (e.g., yeast) into ethanol. The product of fermentation is beer, which comprises a liquid component containing ethanol and water and soluble components, and a solids component containing unfermented particulate matter among other things. The fermentation product is sent to a distillation system. In the distillation system, the fermentation product is distilled and dehydrated into ethanol. The residual matter (e.g., whole stillage) comprises water, soluble components, oil, and unfermented solids (i.e., the solids component of the beer with substantially all ethanol removed that can be dried into dried distillers grains (DDG) and sold as an animal feed product). Other co-products such as syrup and oil contained in the syrup can also be recovered from the stillage. Water removed from the fermentation product in distillation can be treated for reuse at the plant.

In a biorefinery configured to produce ethanol from biomass, ethanol is produced from lignocellulosic material. Lignocellulosic biomass typically comprises cellulose, hemicellulose, and lignin. Cellulose (a type of glucan) is a polysaccharide comprising hexose (C6) sugar monomers such as glucose linked in linear chains. Hemicellulose is a branched chain polysaccharide that may comprise several different pentose (C5) sugar monomers (e.g., xylose and arabinose) and small amounts of hexose (C6) sugar monomers (e.g., mannose, galactose, rhamnose, and glucose) in branched chains.

The biomass is prepared so that sugars in the lignocellulosic material (such as glucose from the cellulose and xylose from the hemicellulose) can be made accessible and fermented into a fermentation product from which ethanol can be recovered. After fermentation, the fermentation product is sent to the distillation system, where the ethanol is recovered by distillation and dehydration. Other bioproducts such as lignin and organic acids may also be recovered as byproducts or co-products during the processing of biomass into ethanol. Determination of how to more efficiently prepare and treat the biomass for production into ethanol will depend upon the source and type or composition of the biomass. Biomass of different types or from different sources is likely to vary in properties and composition (e.g., relative amounts of cellulose, hemicellulose, lignin, and other components). For example, the composition of wood chips will differ from the composition of corn cobs or switchgrass.

It would be advantageous to provide for a system for treatment of biomass to facilitate the production of ethanol. It would also be advantageous to provide for enzyme hydrolysis of C6 and C5 stream. It would further be advantageous to provide for a method for treating biomass to be supplied to a fermentation system for the production of a fermentation product. It would further be advantageous to provide for a system that provides one or more features to facilitate improvement in the efficiency and yield of cellulosic ethanol from biomass.

SUMMARY

The present invention relates to a method for treating biomass to be supplied to a fermentation system for the production of a fermentation product. The method comprises the steps of pre-treating the biomass into pre-treated biomass; separating the pre-treated biomass into a first component comprising glucan and a second component comprising sugars; providing a combined component comprising at least a portion of the first component and at least a portion of the second component; and treating the combined component of the pre-treated biomass into a treated component comprising glucose by application of an enzyme formulation. The biomass comprises lignocellulosic material; the lignocellulosic material comprises at least one of corn cobs, corn plant husks, corn plant leaves, and corn plant stalks. The enzyme formulation comprises a cellulase enzyme. The treated component comprises about 2% to about 15% glucose by weight.

The present invention also relates to a system for treating biomass to be supplied to a fermentation system for the production of a fermentation product. The system comprises an apparatus configured to pre-treat the biomass into pre-treated biomass; a separator configured to separate the pre-treated biomass into a first component comprising glucan and a second component comprising sugars; and a vessel configured to contain a combined component comprising at least a portion of the first component and at least a portion of the second component and to be supplied with an enzyme formulation so that a treated component comprising glucose can be created by enzyme hydrolysis of the combined component. The biomass comprises lignocellulosic material; the lignocellulosic material comprises at least one of corn cobs, corn plant husks, corn plant leaves, and corn plant stalks.

DESCRIPTION OF THE DRAWINGS

FIG. 14A and FIG. 14B list the composition of biomass comprising lignocellulosic plant material from the corn plant according to exemplary and representative embodiments.

FIG. 15A and FIG. 15B list the composition of the liquid component of pre-treated biomass according to exemplary and representative embodiments.

FIG. 16A and FIG. 16B list the composition of the solids component of pre-treated biomass according to exemplary and representative embodiments.

FIG. 17A, FIG. 17B, FIG. 17C, FIG. 18A, FIG. 18B, and FIG. 18C show operating conditions and data/results from the use of the system according to exemplary embodiments.

DETAILED DESCRIPTION

Figure 1A:
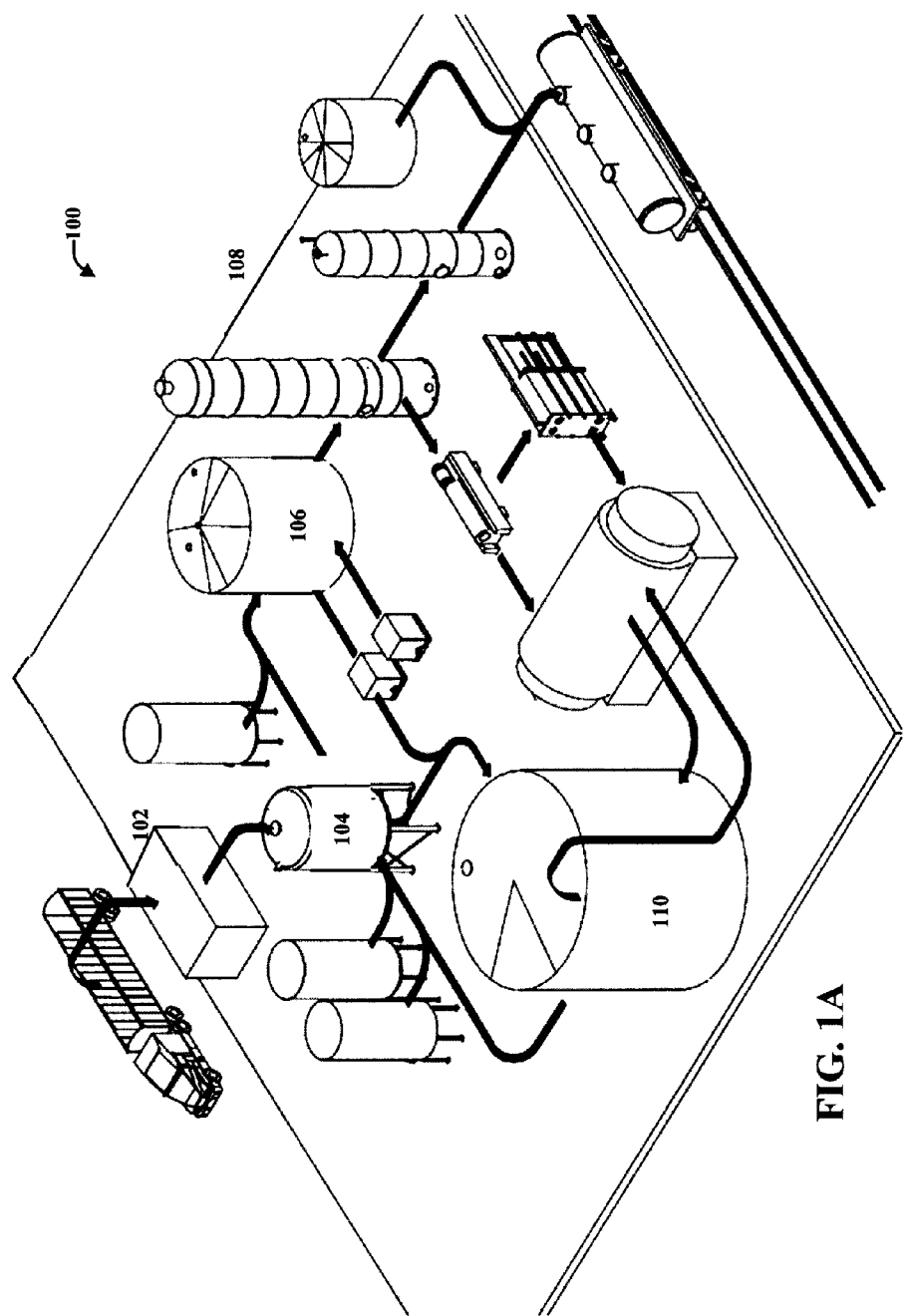
FIG. 1A is a perspective view of a biorefinery comprising a cellulosic ethanol production facility, in accordance with some embodiment.

Referring to FIG. 1A, a biorefinery configured to produce ethanol from biomass is shown at 100.

According to an exemplary embodiment, the biorefinery 100 is configured to produce ethanol from biomass in the form of a lignocellulosic feedstock such as plant material from the corn plant (e.g., corn cobs and corn stover). Lignocellulosic feedstock such as lignocellulosic material from the corn plant comprises cellulose (from which C6 sugars such as glucose can be made available) and/or hemicellulose (from which C5 sugars such as xylose and arabinose can be made available).

As shown in FIG. 1A, the biorefinery comprises an area where biomass is delivered 102 and prepared to be supplied to the cellulosic ethanol production facility 100. The cellulosic ethanol production facility 100 comprises apparatus for preparation, pre-treatment and treatment of the biomass 104 into treated biomass suitable for fermentation into fermentation product in a fermentation system 106. The facility comprises a distillation system 108 in which the fermentation product is distilled and dehydrated into ethanol. As shown in FIG. 1A, the biorefinery may also comprise a waste treatment system 110 (shown as comprising an anaerobic digester and a generator). According to other alternative embodiments, the waste treatment system may comprise other equipment configured to treat, process and recover components from the cellulosic ethanol production process, such as a solid/waste fuel boiler, anaerobic digester, aerobic digester or other biochemical or chemical reactors.

Figure 1B:
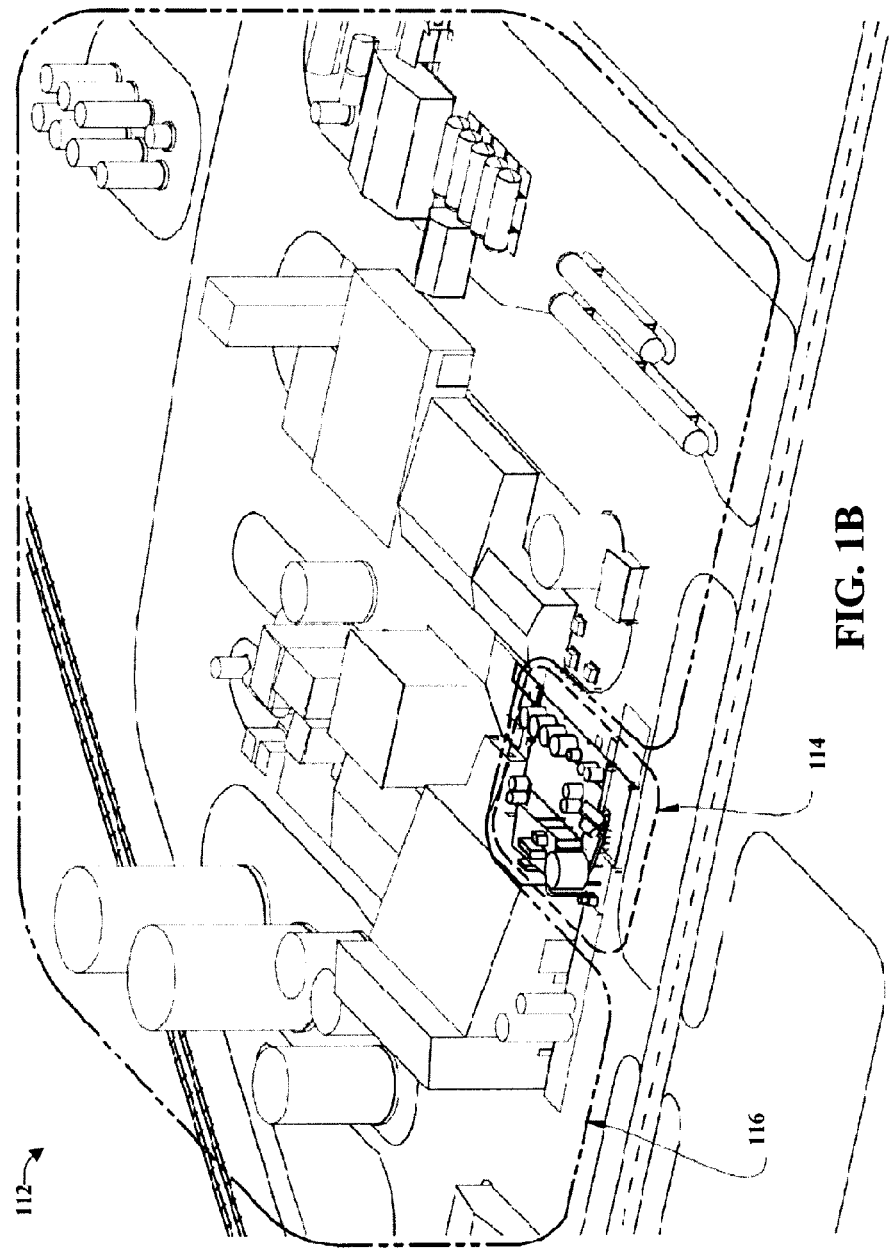
FIG. 1B is a perspective view of a biorefinery comprising a cellulosic ethanol production facility and a corn-based ethanol production facility, in accordance with some embodiment.

As shown in FIG. 1B at 112, according to an exemplary embodiment, a biorefinery may comprise a cellulosic ethanol production facility 114 (which produces ethanol from lignocellulosic material and components of the corn plant) co-located with a corn-based ethanol production facility 116 (which produces ethanol from starch contained in the endosperm component of the corn kernel). As indicated in FIG. 1B, by co-locating the two ethanol production facilities, certain plant systems may be shared, for example, systems for dehydration, storage, denaturing and transportation of ethanol, energy/fuel-to-energy generation systems, plant management and control systems, and other systems. Corn fiber (a component of the corn kernel), which can be made available when the corn kernel is prepared for milling (e.g., by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g., a cellulosic ethanol production facility) may be co-located with other types of plants and facilities, for example an electric power plant, a waste treatment facility, a lumber mill, a paper plant or a facility that processes agricultural products.

Figure 2:
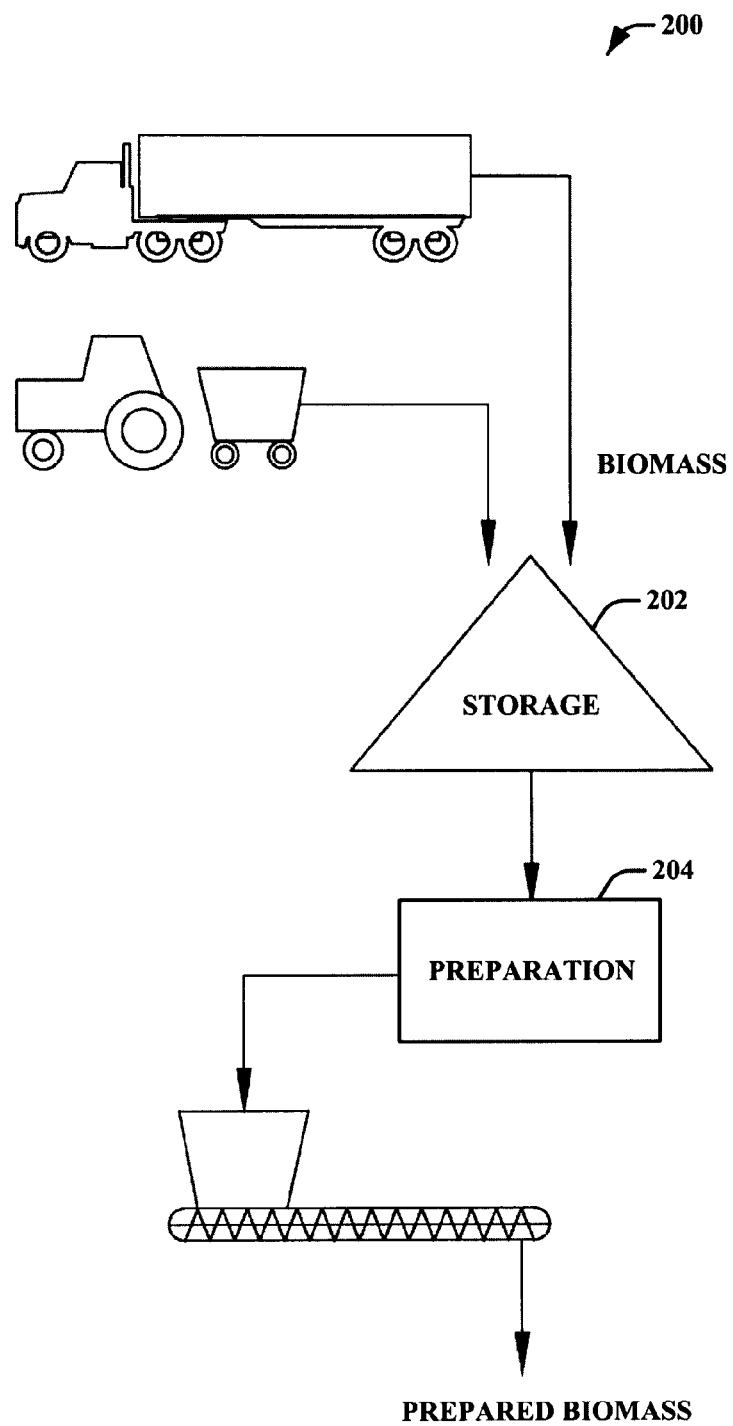
FIG. 2 is a schematic diagram of a system for receipt and preparation of biomass for a cellulosic ethanol production facility, in accordance with some embodiments.

Referring to FIG. 2, a system for preparation of biomass delivered to the biorefinery is shown at 200. The biomass preparation system may comprise apparatus for receipt/unloading of the biomass, cleaning (i.e., removal of foreign matter), grinding (i.e., milling, reduction or densification), and transport and conveyance for processing at the plant.

According to an exemplary embodiment, biomass in the form of corn cobs and stover may be delivered to the biorefinery and stored at a storage location 202 (e.g., in bales, piles, or bins, etc.) and managed for use at the facility. According to an embodiment, the biomass may comprise at least about 20% to about 30% corn cobs by weight with corn stover and other matter. According to other exemplary embodiments, a preparation system 204 of the biorefinery may be configured to prepare any of a wide variety of types of biomass (i.e., plant material) for treatment and processing into ethanol and other bioproducts at the plant.

Figure 3:
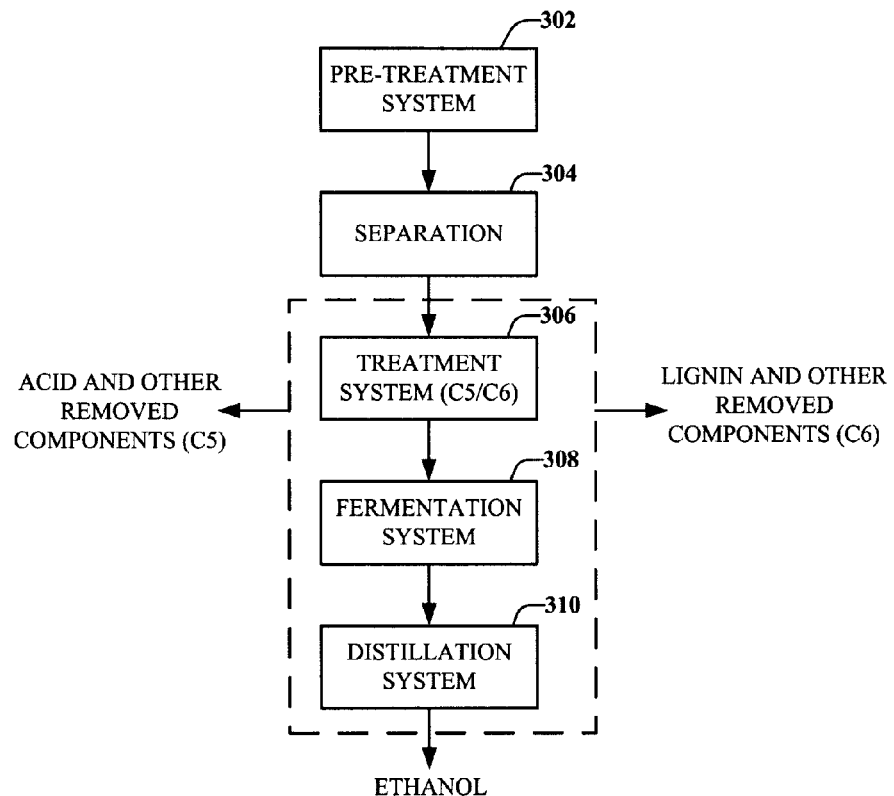
FIG. 3 is a schematic block diagram of a system for the production of ethanol from biomass, in accordance with some embodiments.

Referring to FIG. 3, a schematic flow diagram of a cellulosic ethanol production facility is shown. According to an embodiment, biomass comprising plant material from the corn plant is prepared and cleaned at a preparation system. After preparation, the biomass is mixed with water into a slurry and is pre-treated at a pre-treatment system 302. In the pre-treatment system 302, the biomass is broken down (e.g., by hydrolysis) to facilitate separation 304 into a liquid component (i.e., a stream comprising the C5 sugars) and a solids component (i.e., a stream comprising cellulose from which the C6 sugars can be made available). The C5-sugar-containing liquid component (C5 stream) and C6-sugar-containing solids component (C6 stream) can be treated 306 (as may be suitable) and fermented in a fermentation system 308. Fermentation product from the fermentation system is supplied to a distillation system 310 where the ethanol is recovered.

Figure 4A:
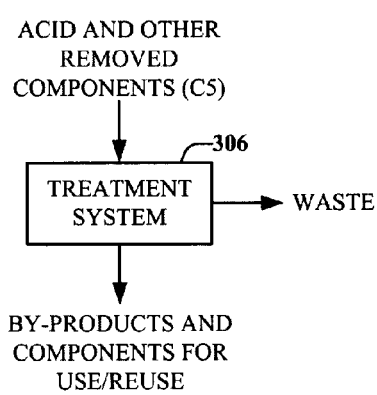
FIG. 4A and FIG. 4B are schematic block diagrams of systems for treatment and processing of components from the production of ethanol from biomass, in accordance with some embodiments.
Figure 4B:
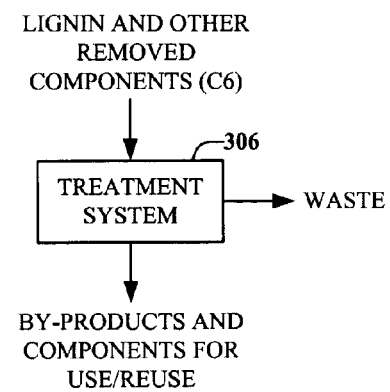

As shown in FIG. 3 and FIG. 4A, removed components from treatment of the C5 stream can be treated or processed, at the treatment system 306, to recover byproducts, such as organic acids and furfural. As shown in FIG. 3 and FIG. 4B, removed components from treatment of the C6 stream, such as lignin or other components, can be treated or processed, at the treatment system 306, into bioproducts or into fuel (such as lignin for a solid fuel boiler or methane produced by treatment of residual/removed matter such as acids and lignin in an anaerobic digester). Generally, components removed during treatment and production of ethanol from the biomass from either or both the C5 stream and the C6 stream (or at distillation) may be processed into bioproducts (e.g., byproducts or co-products) or recovered for use or reuse. For example, removed components from the distillation system (such as stillage or removed solids) or from the treatment of the fermentation product before distillation (e.g., removed solids and particulate matter, which may comprise residual lignin, etc.) can be treated or processed into bioproducts or fuel (e.g., methane produced in an anerobic digester).

According to some embodiments, the biomass comprises plant material from the corn plant, such as corn cobs, husks and leaves and stalks (e.g., at least upper half or three-quarters portion of the stalk); the composition of the plant material (i.e., cellulose, hemicellulose and lignin) will be approximately as indicated in FIG. 14A and FIG. 14B (i.e., after at least initial preparation of the biomass, including removal of any foreign matter). According to some embodiments, the plant material comprises corn cobs, husks/leaves and stalks; for example, the plant material may comprise up to about 100% cobs by weight, up to about 100% husks/leaves by weight, about 50% cobs and approximately 50% husks/leaves by weight, about 30% cobs and about 50% husks/leaves and about 20% stalks by weight, or any of a wide variety of other combinations of cobs, husks/leaves and stalks from the corn plant. See FIG. 14A. According to some embodiments, the lignocellulosic plant material may comprise fiber from the corn kernel (e.g., in some combination with other plant material). FIG. 14B provides ranges believed to be representative of the composition of biomass comprising lignocellulosic material from the corn plant. According to exemplary embodiments, the lignocellulosic plant material of the biomass (from the corn plant) will comprise cellulose at about 30% to about 55% by weight, hemicellulose at about 20% to about 50% by weight, and lignin at about 10% to about 25% by weight; according to exemplary embodiments, the lignocellulosic plant material of the biomass (i.e., cobs, husks/leaves and stalk portions from the corn plant) will comprise cellulose at about 35% to about 45% by weight, hemicellulose at about 24% to about 42% by weight, and lignin at about 12% to about 20% by weight. According to exemplary embodiments, pre-treatment of the biomass will yield a liquid component that comprises xylose at no less than about 1.0% by weight, and a solids component that comprises cellulose (from which glucose can be made available) at no less than about 45% by weight.

Figure 5:
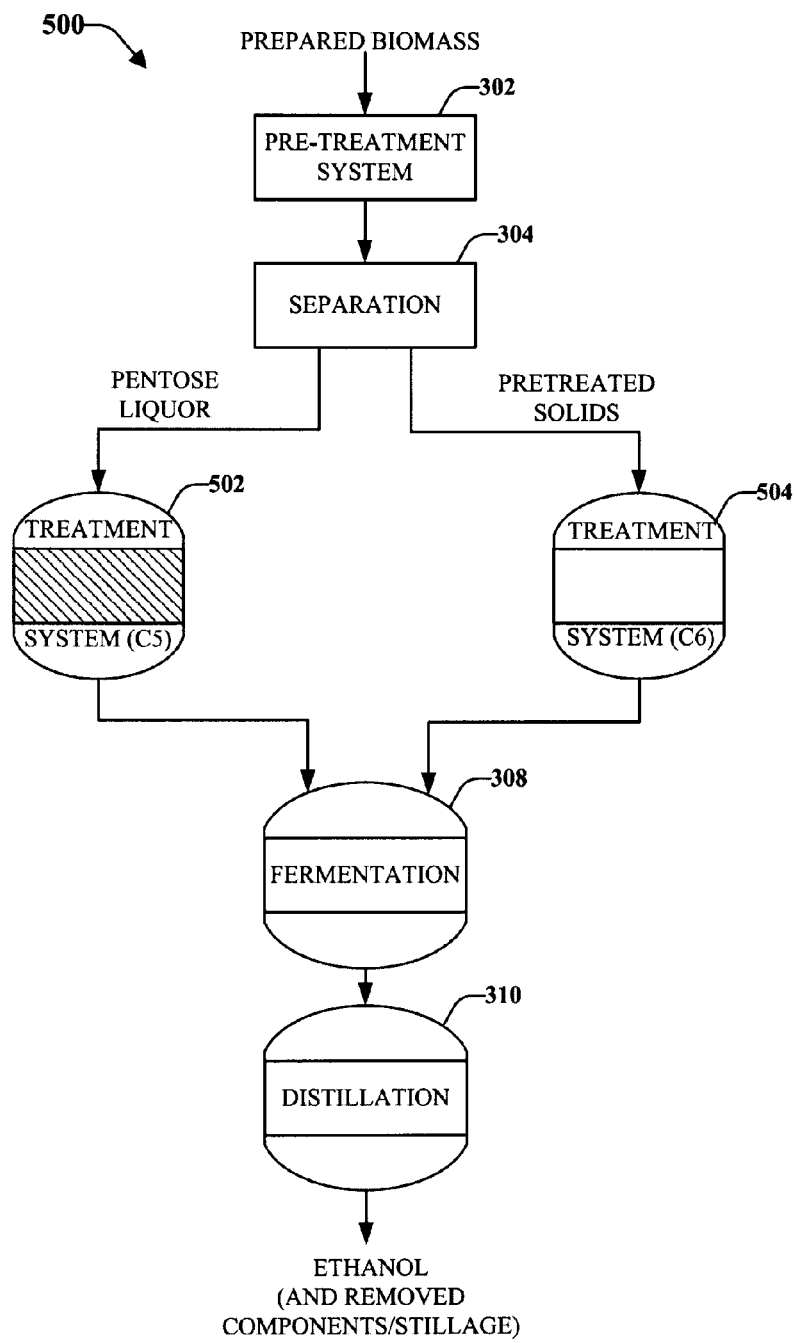
FIG. 5 is a schematic diagram of the process flow for systems for the production of ethanol from biomass, in accordance with some embodiments.

Referring to FIG. 5, exemplary embodiments of systems for the production of ethanol from biomass are shown at 500. Here, biomass is pre-treated in a pre-treatment system 302 and then separated 304 into a liquid component (pentose liquor or C5 stream) and a solids component (C6 stream).

According to some embodiments, in the pre-treatment system an acid will be applied to the prepared biomass to facilitate the breakdown of the biomass for separation into the liquid component (C5 stream from which fermentable C5 sugars can be recovered) and the solids component (C6 stream from which fermentable C6 sugars can be accessed). According to some embodiments, the acid can be applied to the biomass in a reaction vessel under determined operating conditions (e.g., acid concentration, pH, temperature, time, pressure, solids loading, flow rate, supply of process water or steam, etc.), and the biomass can be agitated/mixed in the reaction vessel to facilitate the breakdown of the biomass. According to some embodiments, an acid such as sulfuric acid, hydrochloric acid, nitric acid, phosphoric acid, acetic acid, etc. (or a formulation/mixture of acids) can be applied to the biomass. According to an exemplary embodiment, sulfuric acid will be applied to the biomass in pre-treatment.

The liquid component (C5 stream) typically comprises water, dissolved sugars (such as xylose, arabinose and glucose) to be made available for fermentation into ethanol, acids and other soluble components recovered from the hemicellulose. FIG. 15B provides ranges believed to be representative of the composition of biomass comprising lignocellulosic material from the corn plant. According to an some embodiments, the liquid component may comprise about 5% to about 7% solids (i.e., suspended/residual solids such as partially-hydrolyzed hemicellulose, cellulose, and lignin). According to some embodiments, the liquid component will comprise at least about 2% to about 4% xylose by weight; according to other embodiments, the liquid component will comprise no less than about 1% to about 2% xylose by weight. FIG. 15A and FIG. 15B list the composition of the liquid component of pre-treated biomass prepared from the biomass as indicated in FIG. 14A and FIG. 14B.

The solids component (C6 stream) typically comprises water, acids and solids such as cellulose from which sugar, such as glucose, can be made available for fermentation into ethanol, and lignin. FIG. 16B provides ranges believed to be representative of the composition of biomass comprising lignocellulosic material from the corn plant. According to some embodiments, the solids component may comprise about 10% to about 40% solids by weight after separation; according to some embodiments, the solids component may comprise about 20% to about 30% solids by weight. According to an exemplary embodiment, the solids in the solids component comprise no less than about 30% cellulose, and the solids component may also comprise other dissolved sugars (e.g., glucose and xylose). FIG. 16A and FIG. 16B list the composition of the solids component of pre-treated biomass prepared from biomass as indicated in FIG. 14A and FIG. 14B.

During pre-treatment, the severity of operating conditions (e.g., pH, temperature, and time) may cause formation of components that are inhibitory to fermentation. For example, under some conditions, the dehydration of C5 sugars (e.g., xylose or arabinose) may cause the formation of furfural. Acetic acid may also be formed, for example, when acetate is released during the break down of hemicellulose in pre-treatment. Sulfuric acid, which may be added to prepared biomass to facilitate pre-treatment, if not removed or neutralized, may also be inhibitory to fermentation. According to some embodiments, by adjusting pre-treatment conditions (e.g., pH, temperature, and time), the formation of inhibitors can be reduced or managed; according to other embodiments, components of the pre-treated biomass may be given further treatment to remove or reduce the level of inhibitors or other undesirable matter.

Referring again to FIG. 5, after pre-treatment 302 and separation 304 the C5 stream and the C6 stream are processed separately; as shown, the C5 stream and the C6 stream may be processed separately prior to co-fermentation (i.e., C5/C6 fermentation as shown in FIG. 5) or they may be processed separately including separate fermentation (i.e., separate C5 fermentation and C6 fermentation).

Treatment of the C5 stream (liquid component) of the biomass may be performed at a treatment system 502 in an effort to remove components that are inhibitory to efficient fermentation (e.g., furfural, HMF, sulfuric acid and acetic acid) and residual lignin or other matter that may not be fermentable from the C5 sugar component, so that the sugars (e.g., xylose, arabinose, as well as other sugars such as glucose) are available for fermentation. The C5 sugars in the C5 stream may also be concentrated to improve the efficiency of fermentation (e.g., to improve the titer of ethanol for distillation).

Treatment of the C6 stream (solids component) of the biomass may be performed at a treatment system 504 to make the C6 sugars available for fermentation. According to some embodiments, hydrolysis (e.g., enzyme hydrolysis) may be performed to access the C6 sugars in the cellulose. Treatment may also be performed in an effort to remove lignin and other non-fermentable components in the C6 stream or to remove components such as residual acid or acids that may be inhibitory to efficient fermentation.

According to some embodiments, as shown in FIG. 5, after pre-treatment and separation the C5 stream and the C6 stream can be treated separately and subsequently combined after treatment (e.g., as a slurry) for co-fermentation in a fermentation system 308 to produce a C5/C6 fermentation product from the available sugars (e.g., xylose and glucose). The C5/C6 fermentation product can (after treatment, if any) be supplied to the distillation system 310 for recovery of the ethanol (e.g., through distillation and dehydration). According to other embodiments, the C5 stream and the C6 stream can each be separately processed through fermentation and distillation (after treatment, if any) to produce ethanol. According to some embodiments, a suitable fermenting organism (e.g., ethanologen) may be used in the fermentation system. The selection of an ethanologen may be based on various considerations, such as the predominant types of sugars present in the slurry. Dehydration and/or denaturing of the ethanol produced from the C5 stream and the C6 stream may be performed either separately or in combination.

Figure 6A:
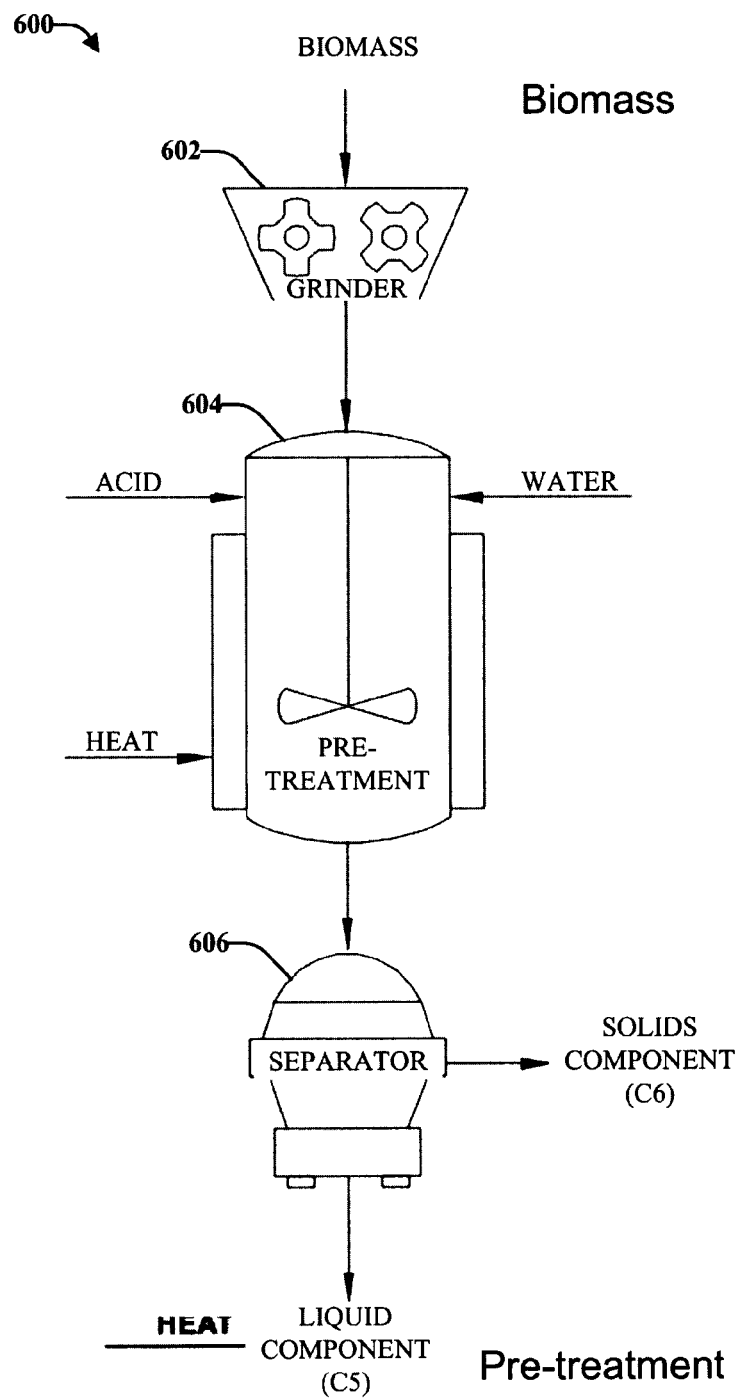
FIG. 6A is a schematic block diagram of an apparatus used for preparation, pre-treatment, and separation of biomass, in accordance with some embodiments.
Figure 6B:
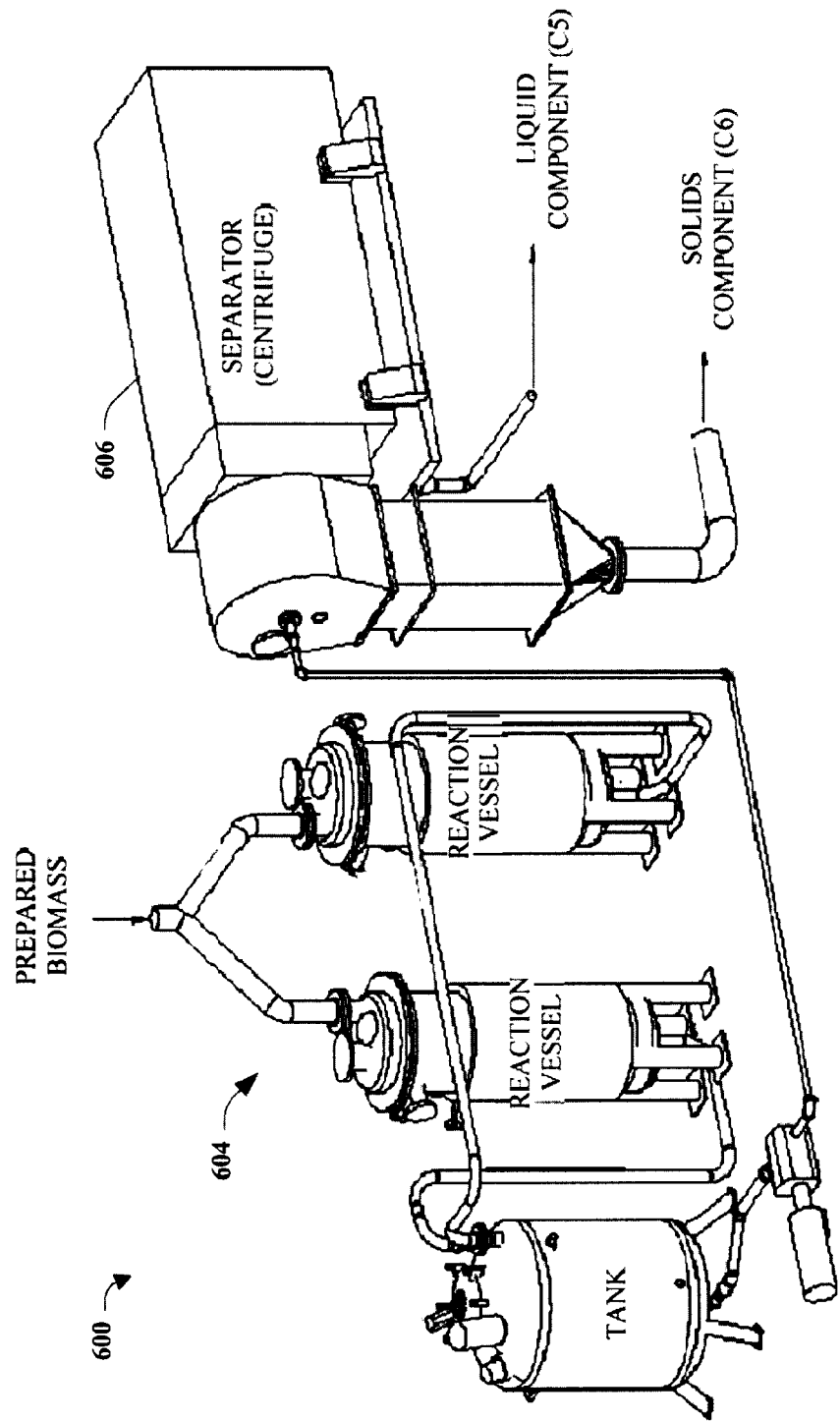
FIG. 6B is a perspective view of an apparatus used to pre-treat and separate the biomass, in accordance with some embodiments.

FIG. 6A and FIG. 6B show the apparatus used for preparation, pre-treatment and separation of lignocellulosic biomass according to an exemplary embodiment, as seen at 600. As shown, biomass is prepared in a grinder 602 (e.g., a grinder or other suitable apparatus or mill). Pre-treatment of the prepared biomass is performed in a reaction vessel 604 (or set of reaction vessels) supplied with prepared biomass and acid/water in a predetermined concentration (or pH) and other operating conditions. As shown in FIG. 6B, the pre-treated biomass can be separated in a centrifuge 606 into a liquid component (C5 stream comprising primarily liquids with some solids) and a solids component (C6 stream comprising liquids and solids such as lignin and cellulose from which glucose can be made available by further treatment).

Figure 7:
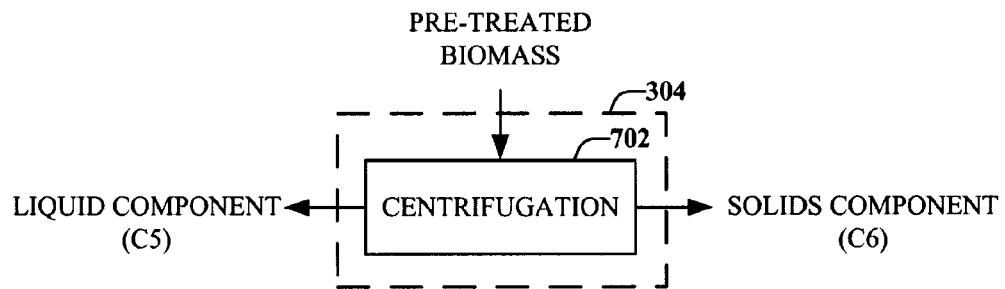
FIG. 7 is a schematic diagram of a process flow for separation of pre-treated biomass according to an exemplary embodiment, in accordance with some embodiments.
Figure 8:
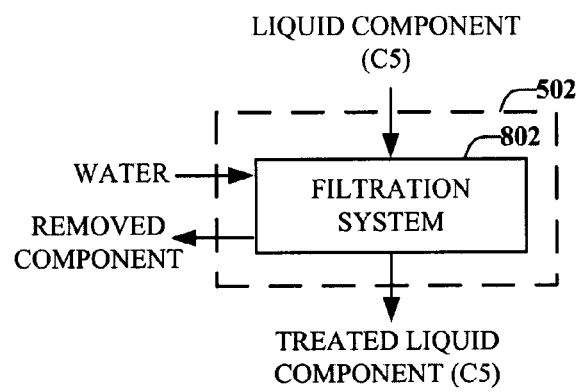
FIG. 8 is a schematic diagram of a treatment system for a component of pre-treated biomass according to an exemplary embodiment.
Figure 10:
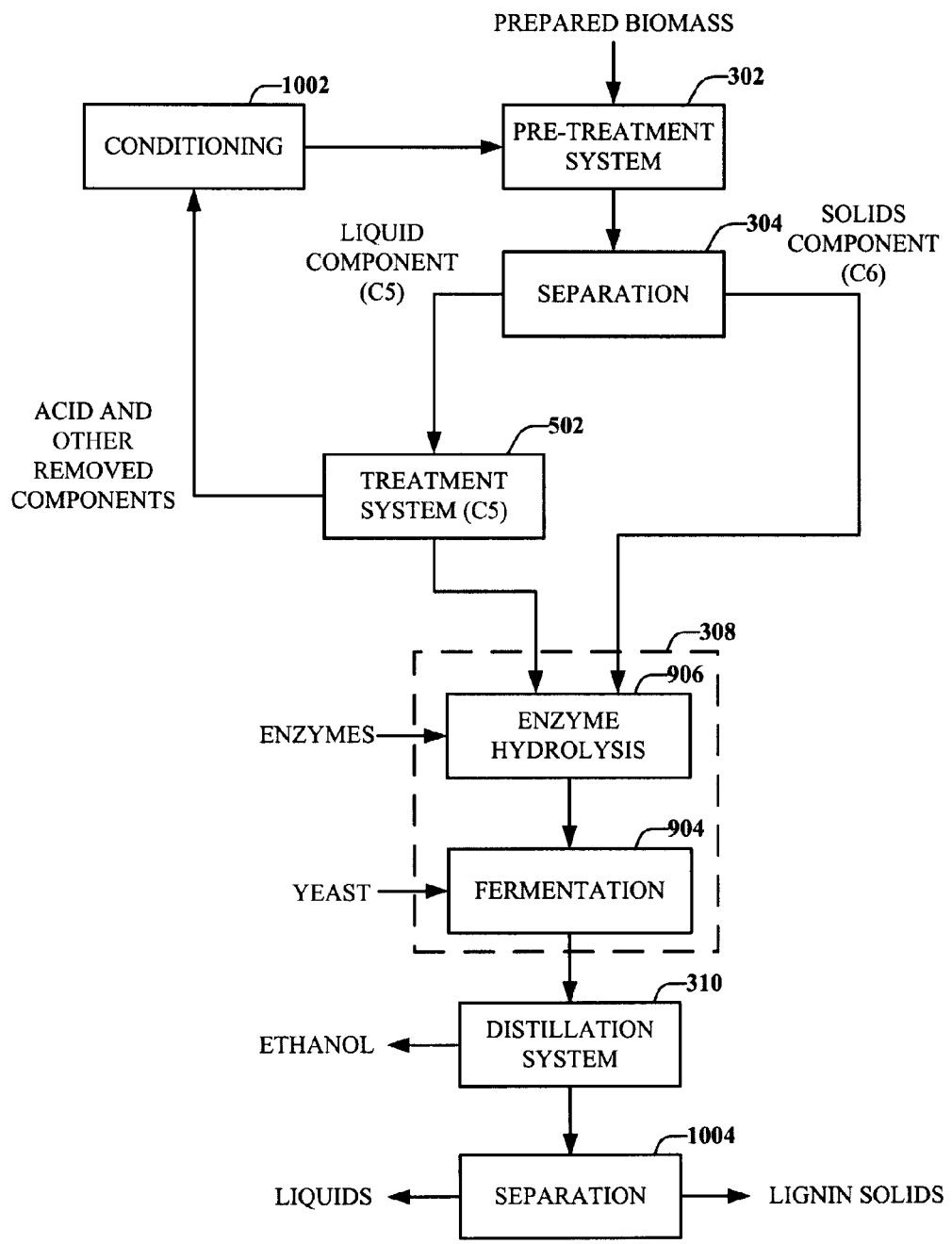
FIG. 10 is a schematic diagram of a process flow for pre-treatment and fermentation of biomass into a fermentation product according to an exemplary embodiment.

As shown in FIG. 7, pre-treated biomass can be separated 304 into a liquid component (C5 stream) and a solids component (C6 stream) using a centrifuge 702, for example, a decanter centrifuge, basket centrifuge, or disc-stack centrifuge. According to other exemplary embodiments, other suitable equipment (such as a hydrocyclone or other type of solid-liquid separator) may be used for the separation of the pre-treated biomass, As shown in FIG. 8 and FIG. 10, the liquid component (i.e., the C5 stream) of the pre-treated biomass can be provided to a treatment system 502. According to an embodiment (see, FIG. 3 and FIG. 4A), during pre-treatment an acid (i.e., dilute sulfuric acid) has been applied to the biomass to facilitate the separation of the biomass into the liquid component (C5 stream) and solids component (C6 stream). As shown in FIG. 8, according to an exemplary embodiment, the treatment system 502 will comprise separation (e.g., using a filtration system 802) of removed components from the C5 stream. Removed components may comprise acids and other matter that may be inhibitory to fermentation (or otherwise undesirable). For example, in the separation of the pre-treated biomass, the sulfuric acid applied in pre-treatment will primarily remain with the liquid component (C5 stream), as well as any acetic acid released from the biomass during pre-treatment; the acidity of the C5 stream (which may have a pH of about 1.5 to 2.0) could be inhibitory to fermentation of the sugars. The treatment system could also be configured to remove other components that are inhibitory to fermentation from the C5 stream, for example, chemicals such as furfural and hydroxymethylfurfural (HMF) that have formed during pre-treatment.

Referring to FIG. 15A and FIG. 15B, according to embodiments where the biomass comprises lignocellulosic material from a corn plant, the liquid component (C5 stream) will comprise water with glucose and xylose available for fermentation, as well as residual solids that may comprise glucan (cellulose) from which glucose can be made available and hemi-cellulose (e.g., xylan) from which xylose can be made available. According to any exemplary embodiment, the C5 stream will comprise at least about 90% water and about 5% to about 7% solids by weight, as well as xylose in a range of about 2% to about 6% by weight and glucose of less than about 1% by weight. According to alternative embodiments, the amount of water and the concentration of sugars (e.g., xylose and glucose) in the C5 stream can be adjusted by treatment (e.g., filtration, evaporation, or dilution). According to some embodiments, the treatment system will prepare the liquid component (C5 stream) for suitable processing in the biorefinery.

Figure 9A:
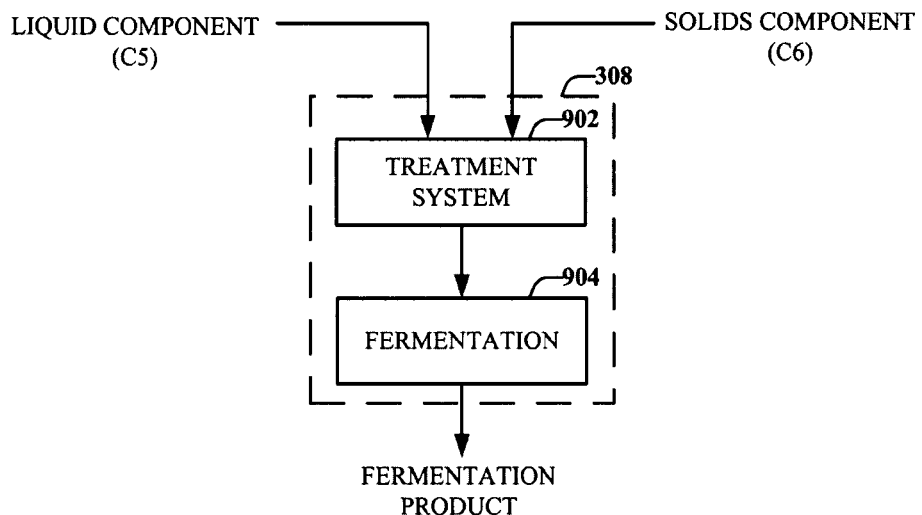
FIG. 9A, FIG. 9B, and FIG. 9C are schematic diagrams of a fermentation system for pre-treated biomass according to exemplary embodiments.
Figure 9B:
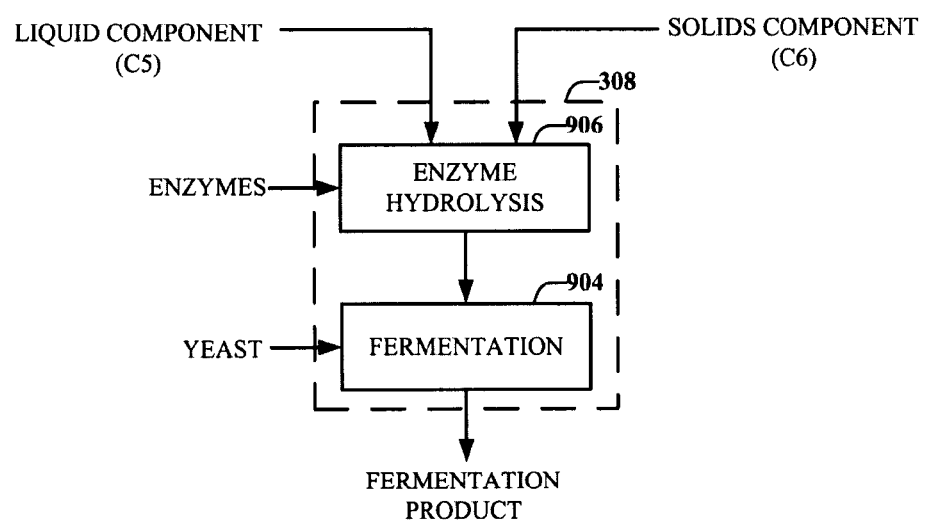
Figure 9C:
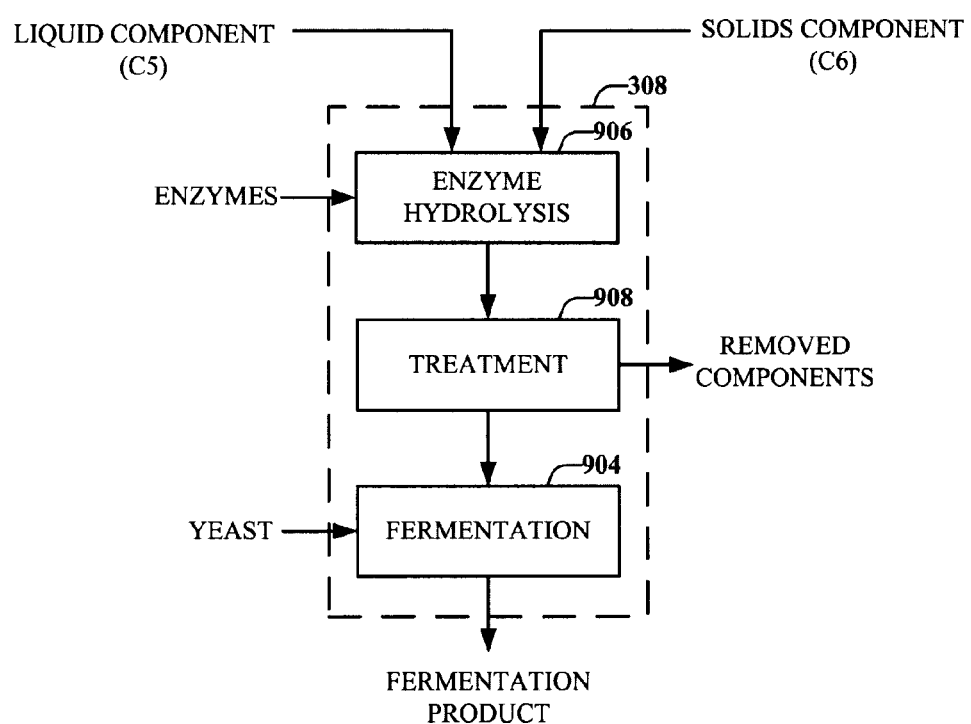

Referring to FIG. 9A, FIG. 9B, and FIG. 9C, the liquid component (C5 stream) and solids component (C6 stream) may be combined into a slurry and supplied to a fermentation system 308 (i.e., for co-fermentation of C5 sugars such as xylose and C6 sugars such as glucose). As shown in FIG. 9A, the fermentation system 308 comprises treatment 902 and fermentation 904 of the combined C5/C6 stream (slurry). Treatment of the combined C5/C6 stream provides a treated C5/C6 stream (e.g., hydrolysate) in which sugars have been made available for fermentation. According to an exemplary embodiment shown in FIG. 9B, the fermentation system 308 comprises treatment of the combined C5/C6 stream by enzyme hydrolysis 906. According to an exemplary embodiment shown in FIG. 9C, the fermentation system 308 may also comprise separation of the hydrolysate (e.g., treated C5/C6 stream) to remove unfermentable matter such as lignin at a treatment 908.

Referring to FIG. 15A and FIG. 15B, according to embodiments where the biomass comprises lignocellulosic material from a corn plant, the solids component (C6 stream) comprises cellulose (e.g., glucan from which fermentable sugars can be accessed), xylan (e.g., partially hydrolyzed hemi-cellulose), lignin and other solid matter, as well as water with other suspended and dissolved solids (which may also comprise fermentable sugars such as xylose and glucose). According to some embodiments, the C6 stream will comprise about 80% to about 90% water and about 5% to about 20% solids by weight. According to some embodiments, the solids component (C6 stream) will be prepared for suitable processing.

As shown in FIG. 5, FIG. 8, FIG. 9C, and FIG. 10, according to some embodiments, treatment may be provided to remove components; for example, removed components may comprise acid from treatment comprising separation performed on the C5 stream (see, e.g., FIG. 5, FIG. 8 and FIG. 10) and lignin from treatment comprising separation performed on the C6 stream (see, e.g., FIG. 5) or hydrolysate (see FIG. 9C). As shown in FIG. 9C, treatment may be provided to concentrate sugars in the hydrolysate (i.e., to remove water). Acid removed from the C5 stream may be conditioned and reused in the pre-treatment system; lignin removed from the C6 stream may be processed into a by-product or fuel. According to alternative embodiments, removed components may be provided to a treatment system such as an anaerobic digester and processed into a fuel (i.e., methane gas). See FIG. 4A and FIG. 4B. As shown in FIG. 10, after treatment (if any) the hydrolysate is supplied to the fermentation system (along with yeast and agents) to produce a fermentation product comprising ethanol that has been fermented from sugars in the hydrolysate.

Additionally, as indicated at FIG. 10, the removed acids from the liquid C5 stream may be conditioned 1002 to recycle acids to the pretreatment system 302. Additionally, after distillation the remaining stillage may be separated 1004 to form a lignin solids and a liquid portion which contains any residual sugars. The liquid portion may be supplied to an anaerobic digester type system for the generation of biogas, or may be recycled as a backset. Lignin solids may be burned as an energy source.

Figure 11:
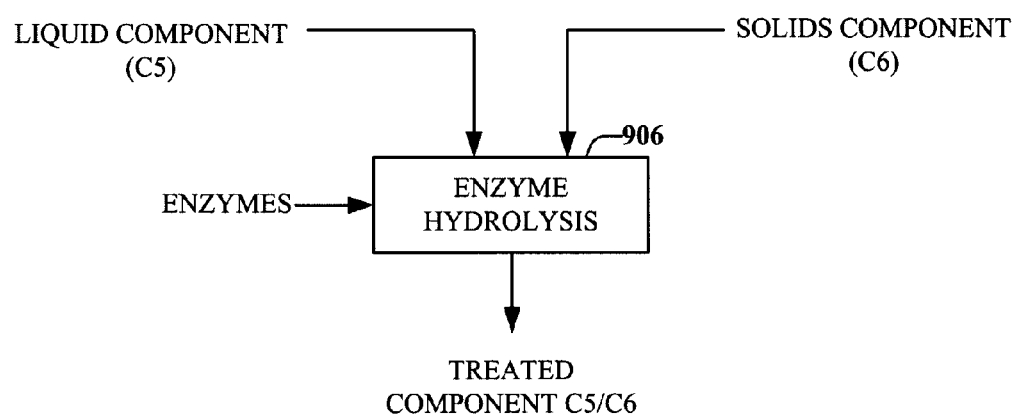
FIG. 11 is a schematic diagram of a system for treatment of pre-treated biomass by enzyme hydrolysis according to an exemplary embodiment.

As shown in FIG. 11, the C6 stream (solids component) and C5 stream (liquid component) of the pre-treated biomass can be supplied as a slurry to a tank (i.e., a temperature-controlled reaction vessel) for enzyme hydrolysis 906. The combined C5/C6 slurry will comprise cellulose (glucan), lignin, xylan, water with dissolved sugars (such as xylose and glucose) and other residual matter from pre-treatment. Residual glucan or xylan present as solids in the liquid component/C5 stream may also become available for enzyme hydrolysis and may supplement the total glucose and xylose yield realized in the hydrolysate. An enzyme formulation is supplied to the slurry; in addition, water and agents may be supplied to the slurry (if necessary, for example, to adjust the solids loading or the pH).

In enzyme hydrolysis, the solids component is treated with an enzyme formulation (e.g., comprising a cellulase enzyme) in a vessel for a period of time to allow for the break down or saccharification by enzyme action of the polymeric cellulose (e.g., polymeric glucan) into accessible monomeric sugars (e.g., monomeric glucose). Agents (e.g., potassium hydroxide or sodium hydroxide for pH adjustment) may also be supplied to the slurry. According to some embodiments, enzyme hydrolysis can be performed using any suitable enzyme or enzyme formulation that will break down cellulose into sugars (e.g., glucose) available for fermentation. According to an exemplary embodiment, the enzyme formulation will comprise a cellulase enzyme. According to any exemplary embodiment, the treated C5/C6 component from enzyme hydrolysis may comprise a hydrolysate in which sugars such as glucose (and xylose) have been made available from the glucan/cellulose (and xylan) and in which dissolved sugars (e.g., such as xylose and glucose) are available.

Figure 12:
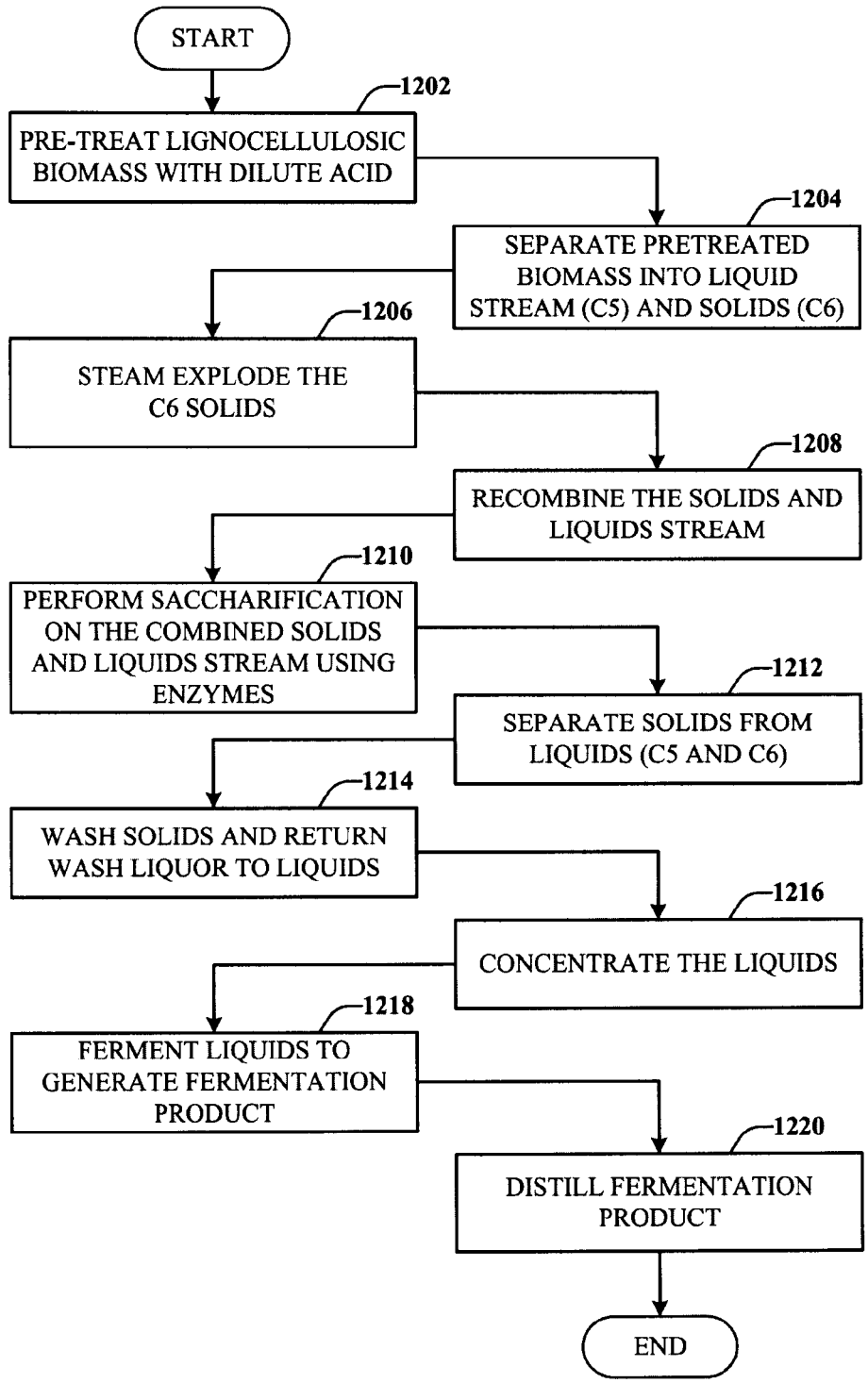
FIG. 12 is an example flowchart for a method of processing biomass for ethanol according to some embodiments.
Figure 13A:
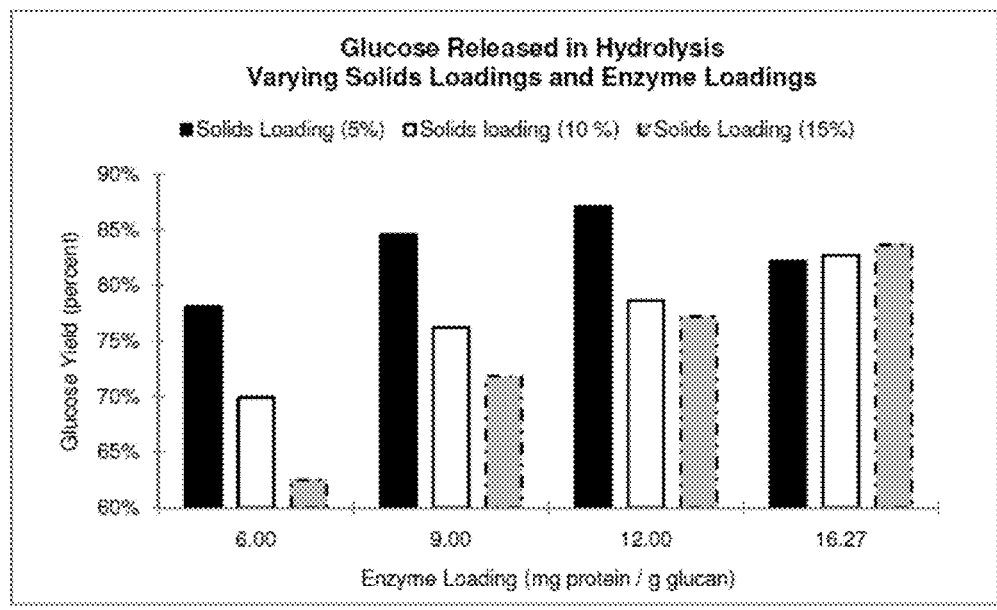
FIG. 13A, FIG. 13B, FIG. 13C, FIG. 13D, and FIG. 13E are graphs of data/results from the use of the system according to exemplary embodiments.
Figure 13B:
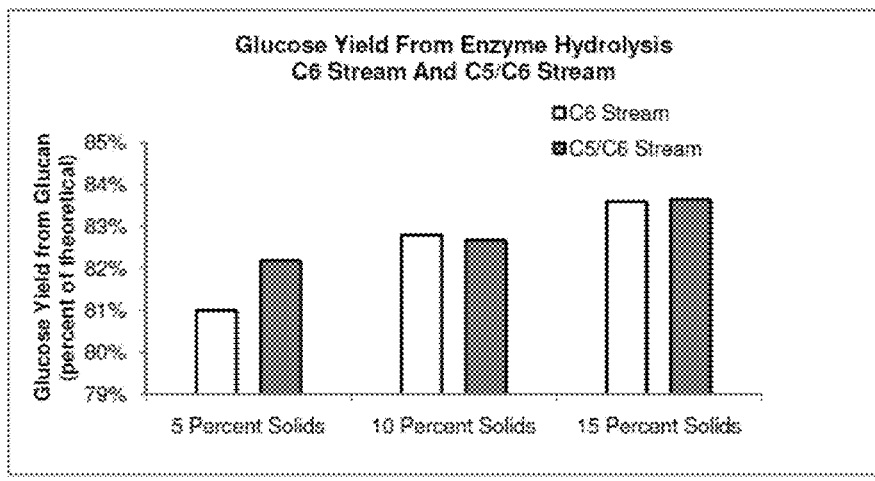
Figure 13C:
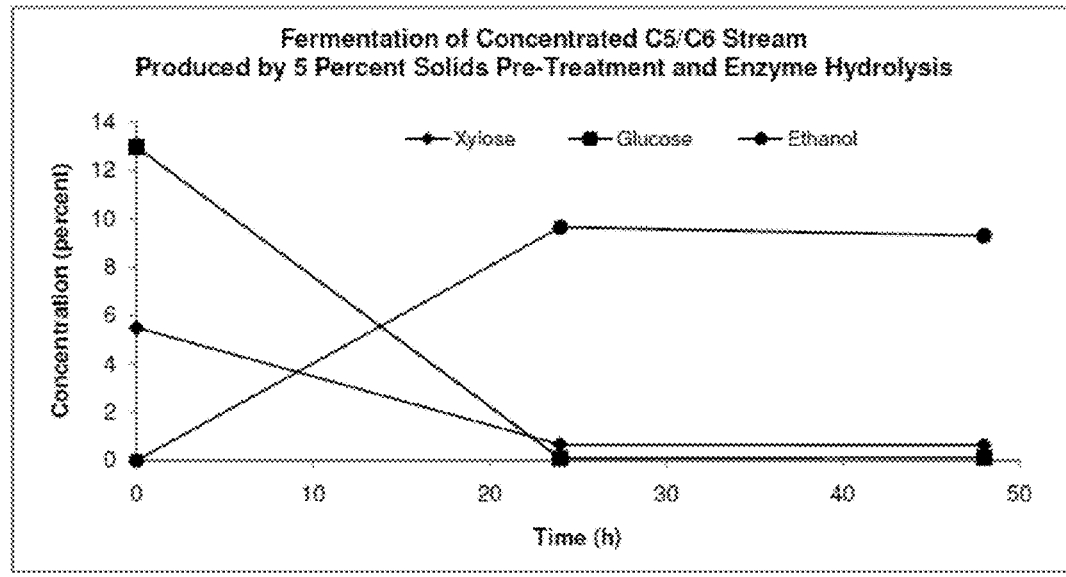
Figure 13D:
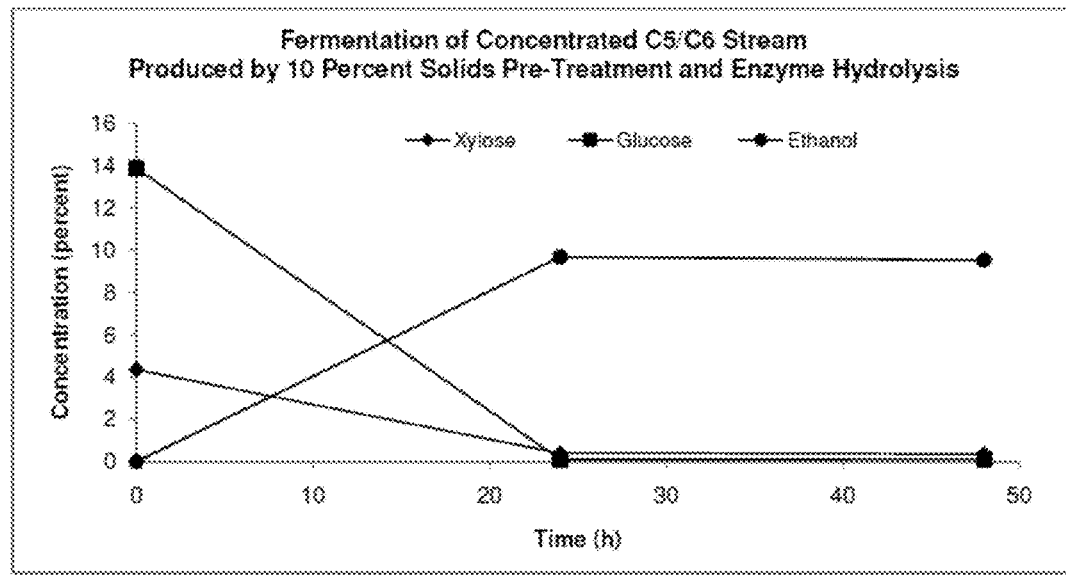
Figure 13E:
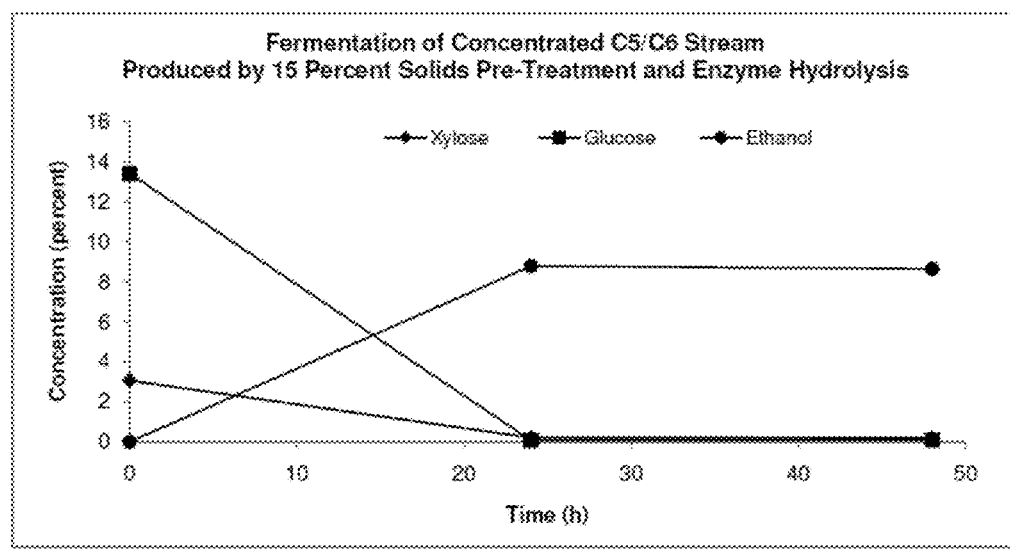

As shown at FIG. 12, an example process flow diagram for the conversion of biomass to ethanol is provided, in accordance with some embodiments. In this process, the biomass is first ground and then pretreated with a dilute acid and heat (at 1202). The pretreated biomass is then separated (at 1204) into a solids and liquid stream. The solid stream comprises primarily lignocellulosic materials, and the liquid portion includes dissolved sugars, such as xylose. The solids are provided to a steam explosion type device (at 1206) to pressurize the solids in the presence of steam (heat). The steam permeates the solids. Then a sudden pressure drop is applied to the solids, releasing the steam and cavitizing the solids. The steam explosion of the solids provides voids and increased surface area in the lignocellulosic material thereby enabling increased accessibility to enzymes for conversion of cellulose to sugar at later steps.

The steam exploded solids and the pentose liquid stream may then be recombined (at 1208). This recombined slurry may then be subjected to a joint saccharification using enzymes, such as cellulase and hemicellulose (at 1210). After enzyme hydrolysis, the resulting solids and the liquids may again be separated (at 1212). The solids at this point comprise mostly of lignin, whereas the liquids include dissolved sugars, including xylose and glucose. The solids (lignin) may be washed to remove any residual sugars (at 1214), and the wash liquor may be added to the liquids.

The liquids may then be concentrated (at 1216) such that the sugar content is high enough to provide a desirable fermentation. The concentrated liquids may then be fermented (at 1218) to generate ethanol. The fermentation product is then distilled (at 1220) to separate out the ethanol from the stillage materials.

Operating conditions for enzyme hydrolysis may comprise the solids loading (ratio of solids to liquid in the slurry), enzyme loading (amount of enzyme formulation as a ratio of enzyme protein to hydrolysable matter such as glucan in the solids fraction), temperature, time, and pH. The solids loading can be adjusted by varying the ratio or proportion of C5 stream (liquid component) which is typically at least about 93% water supplied to the slurry or by supplying additional water to the slurry. The enzyme loading can be adjusted by varying the dose of enzyme formulation relative to the amount of glucan/solids in the treated combined C5/C6 stream. (Glucan/cellulose in the C6 stream is estimated to comprise about 40% to about 60% of the solids on a dry weight basis.) The pH of the slurry can be increased to a suitable level for enzyme hydrolysis for example by application of potassium hydroxide or ammonium hydroxide). Time and temperature can be adjusted by controlling conditions in the reaction vessel.

A typical operating range for solids loading (ratio of solids to liquid in the slurry) is about 5% to about 20% solids dry weight; the more typical range is about 10% to about 17% solids; the exemplary range is about 13% to about 16% solids.

A typical operating range for enzyme loading (i.e., for the cellulase enzyme) is about 4.5 to 18 milligrams of enzyme protein per gram of glucan (dry weight); the more typical range is about 5 to 15 milligrams of enzyme protein per gram of glucan; the exemplary range is about 6 to 12 milligrams of enzyme protein per gram of glucan.

A typical operating temperature range is about 25° C. to 63° C.; the more typical range is about 40° C. to 55° C.; the exemplary range is about 48° C. to 52° C.

A typical pH range is about 4 to 6.3; the more typical range is about 4.5 to 6; the exemplary range is about 5.4 to 5.6.

A typical operating time for enzyme hydrolysis is about 60 to 160 hours; the more typical range is about 70 to 120 hours; exemplary range is about 90 to 110 hours.

According to some embodiments, under operating conditions as indicated above with biomass comprising lignocellulosic material from a corn plant (as indicated in FIG. 14A and FIG. 14B) pre-treated with dilute acid (as indicated in FIG. 5A, FIG. 5B and FIG. 6A) and separated into a solids component (C6 stream) and liquid component (C5 stream) that is combined into a slurry comprising by weight a solids loading of between about 5% and about 15%, and treated by enzyme hydrolysis with a cellulase enzyme at an enzyme loading of between about 4 and about 18 milligrams of enzyme protein per gram of glucan, under operating conditions (as indicated above), a hydrolysate could be produced that provides glucose yields of between about 3.08% and about 10.37% of the theoretical maximum yield (from the estimated available glucan) and xylose. See FIG. 17A, FIG. 17B, and FIG. 17C. The glucose and xylose could be fermented into ethanol. See FIGS. 1 through 11.

An example of the use of the treatment system according to an exemplary embodiment indicates the efficacy of treatment by enzyme hydrolysis of the combined C5/C6 stream from pre-treated biomass to make glucose available for fermentation into ethanol. Results and data from the example are shown in FIGS. 13A through 13E and FIG. 17A, FIG. 17B, FIG. 17C, FIG. 18A, FIG. 18B, and FIG. 18C. The biomass comprised lignocellulosic plant material from the corn plant, see FIG. 14A and FIG. 14B. The biomass had been pre-treated using dilute sulfuric acid and separated into a liquid component (C5 stream) and a solids component (C6 stream), as indicated in FIG. 5A, FIG. 5B, 6A, FIG. 15A, and FIG. 16A, as part of the example, the C5 stream (liquid component comprising water, dissolved sugars and solids) was combined with the C6 stream (solids component comprising glucan from which glucose can be made available as well as other solids and liquid) to adjust the solids loading for enzyme hydrolysis. The enzyme formulation comprised a cellulase enzyme available under the trade name Cellic CTEC from Novozymes North America, Inc. of Franklinton, N.C. Enzymatic hydrolysis was performed at varying levels of enzyme loading (ratio of enzyme protein to glucan/solids). (Glucan/cellulose was estimated to comprise about 60% of the solids in the samples on a dry weight basis.)

EXAMPLE 1

The treatment system was used to evaluate the efficacy of enzymatic hydrolysis to release glucose from the glucan (i.e., cellulose) from pre-treated biomass, as indicated in FIG. 3 and FIG. 11. Samples of slurry were prepared from the solids component/C6 stream and liquid component/C5 stream of the pre-treated biomass. The sample/slurry was adjusted to a pH of about 5.5 (by application of potassium hydroxide). The samples were prepared at different concentrations of total solids by weight: (a) about 5%; (b) about 10%; and (c) about 15%. Enzymatic hydrolysis was performed on subsamples at different enzyme loadings (milligrams of enzyme protein per gram of glucan dry weight): (a) about 6.0 milligrams of enzyme protein; (b) about 9.0 milligrams of enzyme protein; (c) about 12.0 milligrams of enzyme protein; (d) about 16.3 milligrams of enzyme protein. A cellulase enzyme was used. Enzymatic hydrolysis of the subsamples at a temperature of about 50° C. after about 90 hours yielded a hydrolysate comprising glucose and xylose, as indicated in FIG. 18A, FIG. 18B, and FIG. 18C. The glucose yield and xylose yield of the hydrolysate from each of the subsamples was measured and analyzed. The hydrolysate from each sample (i.e., for each of the three levels of solids loading) was combined and evaporated to concentrate the sugars and then fermented and analyzed for sugar conversion and ethanol production (after 24 and 48 hours). It was observed that glucose yields were maximized at higher enzyme loadings but that at a given enzyme loading the glucose yield could be improved by reducing the solids loading (within the indicated operating conditions). It was also observed that efficacy of enzyme hydrolysis could be maintained while using the liquid component/C5 stream to reduce the solids loading (i.e., to dilute the solids component/C6 stream). The results are shown in FIGS. 13A through 13E and FIG. 17A, FIG. 17B, FIG. 17C, FIG. 18A, FIG. 18B, and FIG. 18C.

EXAMPLE 2

After dilute acid hydrolysis, the second pass bale material (which includes corn cobs, leaves, husks, and stalks) was separated into a solids stream which contains the glucan and a liquid stream which is enriched with xylose. The solids stream is referred to as C6 solids and the liquid stream is referred to as C5 liquor. The C6 solids were subjected to steam explosion and then to enzymatic hydrolysis (saccharification). Samples of slurry were prepared for enzymatic hydrolysis at 15% dry C6 solids using the C5 liquor as makeup water. The C5 liquor was concentrated and added back to the solids. This whole broth slurry was pH adjusted to 5.5 using 45% w/w potassium hydroxide. Cellulase enzyme was then added to this pH adjusted slurry at 6 mg enzyme protein per g glucan. The enzymatic hydrolysis of the slurry at 50° C. for 115 hours yielded a hydrolyzate comprising glucose and xylose at 70.7 g/L and 45.9 g/L, respectively. This corresponded to a theoretical glucan to glucose yield of 70.4%. Following the enzymatic hydrolysis, the slurry was cooled to 32° C., pH adjusted to 5.5 using 45% KOH and inoculated with aerobically propagated genetically modified S. cerevisiae at 0.9 g/L (Propagator inoculated at 0.5 g dry yeast/L). Urea (for nutrition) and Lactoside247 (an antimicrobial) were added at 0.24 g/L and 2 ppm, respectively. The fermentation for 48 hours yielded 5.26% v/v ethanol (which corresponded to an efficiency of about 78% sugar to ethanol conversion).

EXAMPLE 3

To improve the efficiency of glucan to glucose conversion in saccharification, the C5 liquor was treated with lime (calcium hydroxide). The C5 liquor was pH adjusted to 3.5 using calcium hydroxide. The precipitate formed was removed by crude centrifugation at 4000 rpm for 1 min. The liquor after separation of solids was concentrated and used as makeup water to prepare 15% dry C6 solids slurry or 18% dry C6 solids slurry. These whole broth slurries were then pH adjusted with ammonium hydroxide to 5.5. Clarified thin stillage (CTS) was included as part of makeup water (25% of total water in makeup for 15% solids slurry or 31% of total water in makeup for 18% solids slurry) to aid in fermentation. These pH adjusted slurries were subjected to enzymatic hydrolysis using the cellulose enzyme at 6 mg enzyme protein per g glucan. After 119 h of enzymatic hydrolysis at 50° C., the hydrolyzate from 15% dry C6 solids showed a glucose and xylose concentrations of 78.8 g/L and 38.9 g/L, respectively; and the hydrolyzate from 18% dry C6 solids showed a glucose and xylose concentrations of 91.3 g/L and 38.8 g/L, respectively. These yields of glucan to glucose corresponded to 78.5 and 75.7% theoretical for 15% C6 solids and 18% C6 solids, respectively. Following the enzymatic hydrolysis, the slurries were cooled to 32° C., pH adjusted to 5.5 using ammonium hydroxide and inoculated with aerobically propagated genetically modified S. cerevisiae at 1.0 g/L (Propagator inoculated at 0.5 g dry yeast/L). Urea (for nutrition) and Lactoside247 (an antimicrobial) were added at 0.24 g/L and 2 ppm, respectively. The fermentation after 24 h yielded 5.55% v/v ethanol (efficiency of 82.4% sugar to ethanol conversion) and 6.07% v/v ethanol (efficiency of 82.9% sugar to ethanol conversion) for 15% C6 solids and 18% C6 solids slurries, respectively.

EXAMPLE 4

The process configuration was slightly altered to avoid the use of lime. Using lime could possibly cause certain issues downstream such as scaling/fouling in the evaporators and also could result in a gypsum waste stream that will have to be dealt with. Therefore, the enzymatic hydrolysis of C6 solids was performed at 18% total C6 solids. Clarified thin stillage (CTS) was included as part of makeup water (31% of total water in makeup) to aid in fermentation. This C6 solids slurry was pH adjusted to 5.5 using ammonium hydroxide. This pH adjusted slurry was subjected to enzymatic hydrolysis using the cellulose enzyme at 6 mg enzyme protein per g glucan. After 119 h of enzymatic hydrolysis at 50° C., the hydrolyzate showed a glucose concentration of 97.5 g/L which corresponded to 80% glucan to glucose conversion. This hydrolyzate was cooled to 32° C. The C5 liquor was concentrated and added to this saccharified hydrolyzate. This mixture was pH adjusted to 5.5 using ammonium hydroxide and inoculated with aerobically propagated genetically modified S. cerevisiae at 1.0 g/L (Propagator inoculated at 0.5 g dry yeast/L). Urea (for nutrition) and Lactoside247 (an antimicrobial) were added at 0.24 g/L and 2 ppm, respectively. The fermentation after 24 h yielded 4.95% v/v ethanol which corresponded to an efficiency of ~81% sugar to ethanol conversion by the yeast.

The embodiments as disclosed and described in the application (including the FIGURES and Examples) are intended to be illustrative and explanatory of the present inventions. Modifications and variations of the disclosed embodiments, for example, of the apparatus and processes employed (or to be employed) as well as of the compositions and treatments used (or to be used), are possible; all such modifications and variations are intended to be within the scope of the present inventions.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

What is claimed is:

1. A method for treating biomass to be supplied to a fermentation system for production of a fermentation product comprising the steps of:
    pre-treating the biomass into pre-treated biomass;
    separating the pre-treated biomass into a first component comprising glucan and a second component comprising glucan and sugars;
    steam exploding the first component;
    providing a combined component comprising at least a portion of the steam exploded first component and at least a portion of the second component;
    treating the combined component of the pre-treated biomass into a treated component comprising glucose by application of an enzyme formulation, wherein the treated component comprises about 2% to about 15% glucose by weight; and
    wherein the biomass comprises lignocellulosic material comprising at least one of corn cobs, corn plant husks, corn plant leaves, and corn plant stalks.

2. The method of claim 1, wherein the treated component comprises a hydrolysate.

3. The method of claim 2, wherein the hydrolysate is treated to increase a concentration of sugars prior to fermentation.

4. The method of claim 2, wherein the first component of the pre-treated biomass comprises about 40% to about 60% glucan by weight and the hydrolysate comprises about 2% to about 15% glucose by weight.

5. The method of claim 1, wherein the treated component comprises hydrolyzed biomass to be supplied to the fermentation system and the fermentation product comprises ethanol.

6. The method of claim 1, wherein the glucan comprises cellulose and the enzyme formulation is capable of converting glucan to glucose.

7. The method of claim 1, wherein the step of pre-treating the biomass is conducted at a temperature in a range of about 25° C. to 63° C. and at a pH of about 4 to 6.3 and for a time of between about 60 and about 160 hours.

8. The method of claim 7, further comprising the step of treating the second component to remove inhibitors.

9. The method of claim 7, further comprising the step of treating the second component to increase a concentration of xylose.

10. The method of claim 7, wherein the combined component comprises about 1% to about 8% glucan.

11. The method of claim 7, wherein the combined component comprises about 1% to about 6% xylan.

12. The method of claim 7, wherein the combined component comprises no less than about 75% water.

13. The method of claim 7, wherein the first component of the pre-treated biomass comprises about 40% to about 60% glucan.

14. The method of claim 7, wherein the step of treating the combined component of the pre-treated biomass is conducted at a temperature in a range of about 47° C. to 53° C. and at a pH of about 5.4 to 5.6 and for a time of between about 90 and about 120 hours.

15. The method of claim 1, wherein the combined component comprises glucose and xylose.

16. The method of claim 15, wherein the combined component comprises glucan and lignin.

17. The method of claim 16, wherein the combined component comprises xylan.

18. The method of claim 1, wherein the combined component comprises at least about 4% solids by weight.

19. The method of claim 18, wherein the combined component comprises at least about 1% glucan by weight.

20. The method of claim 1, wherein the enzyme formulation comprises enzyme protein and is provided to the combined component in a concentration of between about 4.0 and 18 milligrams of the enzyme protein per gram of glucan in the combined component.

21. The method of claim 1, wherein the first component comprises a solids component of the lignocellulosic material.

22. The method of claim 1, wherein the second component comprises a liquid component of the lignocellulosic material.

23. The method of claim 1, wherein the lignocellulosic material consists essentially of corn cobs, corn plant husks, corn plant leaves, and corn stalks.

24. The method of claim 1, wherein the biomass comprises cellulose and further comprising the step of fermenting glucose in the treated component to produce the fermentation product.

25. The method of claim 24, wherein the biomass comprises hemi-cellulose and the fermentation product has been produced by fermentation of xylose.

26. The method of claim 1, wherein the treated component comprises xylose.

27. The method of claim 1, wherein the treated component comprises about 1% to about 4% lignin.

28. The method of claim 1, wherein the step of treating the combined component of the pre-treated biomass is conducted at a temperature in a range of about 40° C. to 55° C. and at a pH of about 1.5 to 6 and for a time of between about 70 and 120 hours.

29. A system for treating biomass to be supplied to a fermentation system for production of a fermentation product comprising:
   an apparatus configured to pre-treat the biomass into pre-treated biomass;
   a separator in fluid communication with the apparatus, wherein the separator is configured to separate the pre-treated biomass into a first component comprising glucan and a second component comprising sugars and glucan;
   a steam explosion device in fluid communication with the separator to receive the first component, wherein the steam explosion device is configured to subject the first component to steam explosion;
   a vessel in fluid communication with the separator and the steam explosion device, wherein the vessel is configured to contain a combined component comprising at least a portion of the steam exploded first component and at least a portion of the second component and to be supplied with an enzyme formulation so that a treated component comprising glucose can be created by enzyme hydrolysis of the combined component;
   wherein the biomass comprises lignocellulosic material; and
   wherein the lignocellulosic material comprises at least one of corn cobs, corn plant husks, corn plant leaves, and corn plant stalks.

30. A method for hydrolyzing lignocellulosic biomass comprising:
   pre-treating the lignocellulosic biomass into pre-treated biomass, wherein pre-treating comprises applying an acid to the lignocellulosic biomass to form a pre-treated biomass;
   separating the pre-treated biomass into a liquid component and a solid component, wherein the liquid component comprises xylose and glucan and solid component comprises glucan;
   steam exploding the solid component;
   combining at least a portion of the steam exploded solid component, at least a portion of the liquid component, and an enzyme formulation to enzymatically hydrolyze the glucan;
   wherein the biomass comprises lignocellulosic material comprising at least one of corn cobs, corn plant husks, corn plant leaves, and corn plant stalks.

* * * * *